(12) United States Patent
Schally et al.

(10) Patent No.: US 8,980,249 B2
(45) Date of Patent: Mar. 17, 2015

(54) AGONISTS OF GROWTH HORMONE RELEASING HORMONE AS EFFECTORS FOR SURVIVAL AND PROLIFERATION OF PANCREATIC ISLETS

(75) Inventors: Andrew V. Schally, Miami, FL (US); Barbara Ludwig, Dresden (DE); Stefan Bornstein, Dresden (DE); Norman L. Block, Miami, FL (US)

(73) Assignees: University of Miami, Miami, FL (US); Dresden University of Technology, Dresden (DE)

( * ) Notice: Subject to any disclaimer, the term of this patent is extended or adjusted under 35 U.S.C. 154(b) by 0 days.

(21) Appl. No.: 13/701,498

(22) PCT Filed: Jun. 3, 2011

(86) PCT No.: PCT/US2011/039162
§ 371 (c)(1),
(2), (4) Date: Feb. 27, 2013

(87) PCT Pub. No.: WO2011/153491
PCT Pub. Date: Dec. 8, 2011

(65) Prior Publication Data
US 2013/0195807 A1   Aug. 1, 2013

Related U.S. Application Data

(60) Provisional application No. 61/351,001, filed on Jun. 3, 2010.

(51) Int. Cl.
*A01N 63/00* (2006.01)
*A01N 65/00* (2009.01)
*C12N 5/00* (2006.01)
*C12N 5/02* (2006.01)
*A61K 38/00* (2006.01)
*A61K 38/28* (2006.01)
*A61P 5/50* (2006.01)
*A61P 3/10* (2006.01)
*A61P 7/12* (2006.01)
*A61K 38/25* (2006.01)
*C07K 14/60* (2006.01)
*A61K 38/24* (2006.01)
*A61K 38/27* (2006.01)
*C07K 14/00* (2006.01)
*C07K 16/00* (2006.01)
*C07K 17/00* (2006.01)
*C07K 1/00* (2006.01)
*A61K 35/12* (2006.01)
*A61K 35/39* (2006.01)

(52) U.S. Cl.
CPC ............ *C07K 14/60* (2013.01); *A61K 35/12* (2013.01); *A61K 38/25* (2013.01); *A61K 35/39* (2013.01)
USPC .......... 424/93.7; 435/375; 514/6.9; 514/11.2; 530/399

(58) Field of Classification Search
CPC ........ A61K 38/00; A61K 38/22; A61K 38/25
See application file for complete search history.

(56) References Cited

U.S. PATENT DOCUMENTS

| | | |
|---|---|---|
| 4,622,312 A | 11/1986 | Felix et al. |
| 4,649,131 A | 3/1987 | Felix et al. |
| 4,689,318 A | 8/1987 | Kaiser et al. |
| 4,784,987 A | 11/1988 | Rivier et al. |
| 4,914,189 A | 4/1990 | Schally et al. |
| 5,262,519 A | 11/1993 | Rivier et al. |
| 5,792,747 A | 8/1998 | Schally et al. |
| 5,846,936 A | 12/1998 | Felix et al. |
| 6,458,764 B1 | 10/2002 | Gravel et al. |
| 7,241,744 B2 | 7/2007 | Draghia-Akli et al. |
| 7,268,113 B2 | 9/2007 | Bridon et al. |
| 7,928,063 B2 | 4/2011 | Izdebski et al. |
| 2005/0261201 A1 | 11/2005 | Polvino et al. |
| 2007/0042950 A1 | 2/2007 | Schally et al. |
| 2009/0023646 A1 | 1/2009 | Gaudreau |
| 2010/0092539 A1 | 4/2010 | Schally et al. |
| 2014/0193378 A1* | 7/2014 | Schally et al. ............... 424/93.7 |

FOREIGN PATENT DOCUMENTS

| | | |
|---|---|---|
| EP | 0413839 | 2/1991 |
| WO | WO 94/11396 | 5/1994 |
| WO | WO 2009/009727 A2 | 1/2009 |

OTHER PUBLICATIONS

Hoglund et al "Growth Hormone Increases Beta-Cell Proliferation in Transplanted Human and Fetal Rat Islets" JOP. J Pancreas (Online) 10:242-248. Published May 18, 2009.*
Izdebski et al "Synthesis and biological evaluation of superactive agonists of growth hormone-releasing hormone" PNAS 92:4872-4876. Published May 1995.*
Höglund et al "Growth Hormone Increases Beta-Cell Proliferation in Transplanted Human and Fetal Rat Islets" JOP. J Pancreas 10:242-248, published May 18, 2009.*
Izdebski et al "Synthesis and biological evaluation of superactive agonists of growth hormone-releasing hormone" PNAS 92:4872-4876, published May 23, 1995.*
Wang and Tomlinson "Tesamorelin, a human growth hormone releasing factor analogue" Exp. Opin. Investig. Drugs 18:303-310. Published Mar. 2009.*
Hu et al "Effect of Human Growth Hormone on the Proliferation of Human Fetal Islet Cells in Vitro" Chinese Medical Journal 105:721-725. Published 1992.*
Schubert et al "Transplantation of pancreatic islets to adrenal gland is promoted by agonists of growth-hormone-releasing hormone" Proc. Nat. Acad. Sci. 110:2288-2293. Published Feb. 5, 2013.*

(Continued)

*Primary Examiner* — James H Alstrum Acevedo
*Assistant Examiner* — Zachary J Miknis
(74) *Attorney, Agent, or Firm* — Pepper Hamilton LLP

(57) ABSTRACT

Agonists of growth hormone releasing hormone promote islet graft growth and proliferation in patients. Methods of treating patients comprise the use of these agonists.

8 Claims, 7 Drawing Sheets

(56) References Cited

OTHER PUBLICATIONS

Bajusz, et al. in *Peptides*, 1982, Blaha and Melon, Eds. de Gruyter, Berlin-N.Y., 1983, pp. 643-647.
Cai, et al., "Synthesis of new potent agonistic analogs of growth hormone-releasing hormone (GHRH) and evaluation of their endocrine and cardiac activities," *Peptides* (Feb. 2014), 52:104-112. Epub: Dec. 25, 2013.
Campbell, et al., "GRF analogs and fragments: Correlation between receptor binding, activity and structure," *Peptides* (May/Jun. 1991), 12(3):569-574.
Corpas, et al., "Growth Hormone (GH)-Releasing Hormone-(1-29) Twice Daily Reverses the Decreased GH and Insulin-Like Growth Factor-I Levels in Old Men," *J. Clin. Endocrin. Metabol.* (1992), 75, 530-535.
Falutz, et al., "Effects of Tesamorelin, a Growth Hormone-Releasing Factor, in HIV_Infected Patients with Abdominal Fat Accumulation: A Randomized Placebo-Controlled Trial With a Safety Extension," *Acquir Immune Defic Syndr.* (2010), 53: 311-322.
Felix, et al., "Synthesis, biological activity and conformational analysis of cyclic GRF analogs," *Int. J. Peptide Protein Res.* (Dec. 1988), 32(6): 441-454.
Ferninandi, et al., "Non-Clinical Pharmacology and Safety Evaluation of TH9507, a Human Growth Hormone-Releasing Factor Analogue," *Basic & Clin Pharmacol Toxicol.* (2007), 100: 49-58.
Frohman, et al., "Dipeptidylpeptidase IV and Trypsin-like Enzymatic Degradation of Human Growth Hormone-releasing Hormone in Plasma," *J. Clin. Invest.* (1989), 83, 1533-1540.
Izdebski, et al., "Synthesis and biological evaluation of superactive agonists of growth hormone-releasing hormone," *Proc Natl Acad Sci USA*, (May 1995), 92:4872-4876.
Kirk, et al., "Treatment with GHRH(1-29)NH2 in children with idiopathic short stature induces a sustained increase in growth velocity," *Clinical Endocrinol.* (Oct. 1994) 41(4):487-493.
Kovacs, et al., "An evaluation of intravenous, subcutaneous, and in vitro activity of new agmatine analogs of growth-hormone releasing hormone hGH-RW (1-29)NH2," *Life Science*, (1988), 42(1): 27-35.
Merrifield, "Solid Phase Peptide Synthesis. I. The Synthesis of a Tetrapeptide," *J.Am.Chem.Soc.*, (1963), 85:2149.
Muranishi, et al., "Lipophilic Peptides: Synthesis of Lauroyl Thyrotropin-Releasing Hormone and Its Biological Activity," *Pharm. Res.* (May 1991), 8(5)649-652.
Ross, et al., "Treatment of Growth-Hormone Deficiency with Growth-Hormone-Releasing Hormone," *Lancet 1* (Jan. 3, 1987), 8523:5-8.
Takano et al., "Human growth hormone-releasing hormone (hGH-RH; hGRF) treatment of four patients with GH deficiency," *Endocrinol. Japan* (1988) 35(5); 775-781.
Thorner, et al., "Acceleration of Growth in Two Children Treated with Human Growth Hormone-Releasing Factor," *N. Engl. J. Med.* (Jan. 3, 1985), 312(1):4-9.
Vance, "Growth hormone for the elderly?," *N. Eng. J. Med* (1990), 323(1):52-54.
Zarandi, et al., "Synthesis and in vitro and in vivo activity of analogs of growth hormone-releasing hormone (GH-RH) with C-terminal agmatine," *Int. J. Peptide Protein Res.* (Dec. 1990), 36(6):499-505.
Armann et al., Quantification of basal and stimulated ROS levels as predictors of islet potency and function, *Am J Transplant*, (2007), 7:38-47.
Bonner-Weir, In vitro cultivation of human islets from expanded ductal tissue, *Proc Natl Acad Sci USA*, (Jul. 5, 2000), 97(14):7999-8004.
Dor et al., Adult pancreatic B-cells are formed by self-duplication rather than stem-cell differentiation, *Nature*, (May 6, 2004), 429:41-44.
Fiaschi-Taesch et al., Hepatocyte Growth Factor Enhances Engraftment and Function of Nonhuman Primate Islets, *Diabetes*, (Oct. 2008), 57:2745-2754.
Granata et al., Obestatin promotes survival of pancreatic beta-cells and human islets and induces expression of genes involved in the regulation of beta-cell mass and function, *Diabetes*, (Apr. 2008), 57:967-979.
Granata et al., Growth hormone-releasing hormone promotes survival of cardiac myocytes in vitro and protects against ischaemia-reperfusion injury in rat heart, *Cardiovasc Res*, (2009), 83:303-312.
Guarcello et al., Growth hormone releasing hormone receptors on thymocytes and splenocytes from rats, *Cell Immunol*, (1991), 136:291-902.
Havt et al., The expression of the pituitary growth hormone-releasing hormone receptor and its splice variants in normal and neoplastic human tissues, *Proc Natl Acad Sci USA* (Nov. 29, 2005), 102(48):17424-17429.
Huising et al., CRFR1 is expressed on pancreatic B cells, promotes B cell proliferation, and potentiates insulin secretion in a glucose-dependent manner, *Proc Natl Acad Sci USA*, (Jan. 12, 2010), 107(2): 912-917.
Jabs et al., Reduced insulin secretion and content in VEGF-a deficient mouse pancreatic islets, *Exp Clin Endoctrinol Diabetes* (2008), 116 Suppl. 1:S45-49.
Kanashiro-Takeuchi et al., Cardioprotective effects of growth hormone-releasing hormone agonist after myocardial infarction, *Proc Natl Adac Sci USA*, (Feb. 9, 2010), 107(6):2604-2609.
Khorram et al., Effects of [Norleucine27] Growth Hormone-Releasing Hormone (GHRH) (1-29)-NH2 Administration on the Immune System of Aging Men and Women, *J Clin Endocrinol Metab*, (1997), 82(11):3590-3596.
Lehmann et al., Has time come for new goals in human islet transplantation?, *Am J Transplant*, (2008), 8:1096-1100.
Letsch et al., Growth hormone-releasing hormone (GHRH) antagonists inhibit the proliferation of androgen-dependent and -independent prostate cancers, *Proc Natl Adac Sci USA*, (Feb. 4, 2003), 100(3):1250-1255.
Ling et al., Isolation, primary structure, and synthesis of human hypothalamic somatocrini: growth hormone-releasing factor. *Proc Natl Acad Sci USA*, (1984), 81:4302-4306.
Nielsen et al., Beta cell proliferation and growth factors, *J. Mol. Med.* (1999), 77:62-66.
Rekasi et al., Isolation and sequencing of cDNAs for splice variants of growth hormone-releasing hormone receptors from human cancers, *Proc Natl Acad Sci USA*, (Sep. 12, 2000), 97(19):10561-10566.
Schally et al., Agonistic Analogs of Growth Hormone-Releasing Hormone: Endocrine and Growth Studies, *Growth Hormone Secretagogues in Clinical Practice* (1998), eds. Bercu and Walker, (Marcel Dekker, Inc. New York), 131-143.
Shapiro et al., International trial of the Edmonton protocol for islet transplantation, *N Engl J Med*, (2006), 355:1318-1330.
Vance, Growth-Hormone-Releasing Hormone, *Clin Chem*, (1990), 36:415-420.
Vasavada et al., Growth factors and beta cell replication, *Int J. Biochem Cell Biol, Epub 31*, (Aug. 2005), 38(5-6):931-950.
Ziegler et al., Dehydroepiandrosterone induces a neuroendocrine phenotype in nerve growth factor-stimulated chromaffin pheochromocytoma PC12 cells, *Endocrinology*, (2008), 149:320-328.
Ziegler et al., Expression of neuropeptide hormone receptors in human adrenal tumors and cell lines: Antiproliferative effects of peptide analogues, *Proc Natl Acad Sci USA*, (Sep. 15, 2009), 106(37):15879-15884.
International Search Report for PCT/US2011/039162 dated Feb. 29, 2012.

\* cited by examiner

_US 8,980,249 B2_

SEQUENCE LISTING

<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: synthetic peptide of GHRH
<220> FEATURE:
<221> NAME/KEY: MISC_FEATURE
<222> LOCATION: (1)..(1)
<223> OTHER INFORMATION: Xaa is Ala, Abu or Aib where the N end is
      modified by an omega or an alpha-omega substituted alkyl group.
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Asn, Ser, Gln or Thr
<220> FEATURE:
<221> NAME/KEY: MISC_FEATURE
<222> LOCATION: (11)..(11)
<223> OTHER INFORMATION: Xaa is Lys or Orn
<220> FEATURE:
<221> NAME/KEY: MISC_FEATURE
<222> LOCATION: (12)..(12)
<223> OTHER INFORMATION: Xaa is Val or Ile
<220> FEATURE:
<221> NAME/KEY: MISC_FEATURE
<222> LOCATION: (14)..(14)
<223> OTHER INFORMATION: Xaa is Ala, Gly or Abu
<220> FEATURE:
<221> NAME/KEY: MISC_FEATURE
<222> LOCATION: (20)..(20)
<223> OTHER INFORMATION: Xaa is Lys or Orn
<220> FEATURE:
<221> NAME/KEY: MISC_FEATURE
<222> LOCATION: (21)..(21)
<223> OTHER INFORMATION: Xaa is Leu, Ala or Abu
<220> FEATURE:
<221> NAME/KEY: MISC_FEATURE
<222> LOCATION: (22)..(22)
<223> OTHER INFORMATION: Xaa is Leu, Ala or Abu
<220> FEATURE:
<221> NAME/KEY: MISC_FEATURE
<222> LOCATION: (24)..(24)
<223> OTHER INFORMATION: Xaa is Asp or Glu
<220> FEATURE:
<221> NAME/KEY: MISC_FEATURE
<222> LOCATION: (26)..(26)
<223> OTHER INFORMATION: Xaa is Met, Nle, Ile or Leu
<220> FEATURE:
<221> NAME/KEY: MISC_FEATURE
<222> LOCATION: (27)..(27)
<223> OTHER INFORMATION: Xaa is Asp, Asn or Ser where the C end is
      modified by a lower omega-guanidino alkyl group.

<400> SEQUENCE: 1

Xaa Xaa Ala Ile Phe Thr Xaa Ser Tyr Arg Xaa Xaa Leu Xaa Gln Leu
1               5                   10                  15

Ser Ala Arg Xaa Xaa Xaa Gln Xaa Ile Xaa Xaa
            20                  25

<210> SEQ ID NO 2
<211> LENGTH: 27
<212> TYPE: PRT
<213> ORGANISM: Artificial Sequence
<220> FEATURE:
<223> OTHER INFORMATION: synthetic peptide of GHRH
<220> FEATURE:
<221> NAME/KEY: MISC_FEATURE
<222> LOCATION: (1)..(1)
<223> OTHER INFORMATION: Ala is modified at the N end by an omega or

```
                an alpha-omega substituted alkyl group.
<220> FEATURE:
<221> NAME/KEY: MISC_FEATURE
<222> LOCATION: (7)..(7)
<223> OTHER INFORMATION: Xaa is Asn, Ser, Gln or Thr
<220> FEATURE:
<221> NAME/KEY: MISC_FEATURE
<222> LOCATION: (11)..(11)
<223> OTHER INFORMATION: Xaa is Lys or Orn
<220> FEATURE:
<221> NAME/KEY: MISC_FEATURE
<222> LOCATION: (14)..(14)
<223> OTHER INFORMATION: Xaa is Ala, Gly or Abu
<220> FEATURE:
<221> NAME/KEY: MISC_FEATURE
<222> LOCATION: (20)..(20)
<223> OTHER INFORMATION: Xaa is Lys or Orn
<220> FEATURE:
<221> NAME/KEY: MISC_FEATURE
<222> LOCATION: (26)..(26)
<223> OTHER INFORMATION: Xaa is met, Nle, Ile or Leu
<220> FEATURE:
<221> NAME/KEY: MISC_FEATURE
<222> LOCATION: (27)..(27)
<223> OTHER INFORMATION: Xaa is Asp, Asn or Ser, where the C end is
        modified by a lower omega-guanidino alkyl group.

<400> SEQUENCE: 2

Ala Asp Ala Ile Phe Thr Xaa Ser Tyr Arg Xaa Val Leu Xaa Gln Leu
1               5                   10                  15

Ser Ala Arg Xaa Leu Leu Gln Asp Ile Xaa Xaa
            20                  25
```

AGONISTS OF GROWTH HORMONE RELEASING HORMONE AS EFFECTORS FOR SURVIVAL AND PROLIFERATION OF PANCREATIC ISLETS

STATEMENT REGARDING FEDERALLY SPONSORED RESEARCH

Dr. Andrew Schally is an employee of the United States government. The U.S. government may have certain rights in the invention.

INCORPORATION OF SEQUENCE LISTING

A computer readable form of the sequence listing "SubSequenceListing_ST25.txt" (2,567 bytes) submitted via EFS-WEB and created on Apr. 4, 2013, is herein incorporated by reference.

FIELD OF THE INVENTION

Embodiments of the invention provide for agonists of growth hormone releasing hormone and methods of treatment of diseases by agonists of growth hormone releasing hormone.

BACKGROUND

Transplantation of pancreatic islet cells is a valid treatment option for selected patients with diabetes. Under current protocols, the main therapeutic goal that can be reliably achieved is improved glycemic control and prevention of severe hypoglycemic episodes. Insulin independence can only be achieved for a limited time after repeated transplantations (1) due to insufficient islet mass and progressive loss of islets over time. Therefore, efforts to improve islet transplantation focus on improving the exploitation of mechanisms governing beta cell proliferation and growth as well as islet quality (2-4).

Several growth factors that may have potential for enhancing beta cell mass have been identified (5). A natural growth factor-mediated adaptation of islet cell mass occurs due to increased demand during pregnancy as well as with obesity (6). In addition, promotion of islet cell growth has been linked to glucagon-like peptide 1 (GLP-1), obestatin and ghrelin (4, 7, 8). Surprisingly, little attention has been given to the possible role of growth hormone-releasing hormone or its agonists. In his Nobel lecture more than 60 years ago, Bernardo Houssay described the critical role of the "hypophysis in carbohydrate metabolism and in diabetes" (9). He observed that extracts of the anterior pituitary gland can produce a stimulation and hyperplasia of islets under certain conditions. With the advent of stem cell biology and regenerative medicine, there has now been a renewed interest in elucidating the role of hypothalamic-pituitary-growth factors in islet cell regulation.

Growth-hormone-releasing-hormone (GHRH) stimulates the release of growth hormone (GH) from the pituitary and has been the focus of intense studies since its structure was described in 1982 (10, 11). The full biological activity of GHRH resides in the N-terminal 1-29 amino acid sequence of this peptide (12). GHRH and the pituitary type of GHRH-receptor as well as its splice variants are expressed in many human tissues, i.e. ovary, testis, pancreas, colon, esophagus, breast, kidney, liver, prostate, lungs and thymus (13-15).

A recent study has shown that rat GHRH promoted survival of cardiomyocytes in vitro and protected rat hearts from ischemia-reperfusion injury (16). The detection of the GHRH receptor (GHRH-R) on the cardiomyocyte sarcolemma supports the view that GHRH may elicit direct signal transduction within the heart, independent of the GH/IGF-1 axis per se (17). Synthetic GHRH agonists, such as JI-34, JI-36, JI-38 (GHRH-A), are more potent and longer-acting than native GHRH (18, 19). Recently, it was demonstrated that GHRH-agonist JI-38 has a favorable cardiac effect, attenuating infarct size as well as the progressive decrease of cardiac structure and function following myocardial infarction (MI) (16).

SUMMARY

Embodiments of the invention comprise administration of GHRH and/or at least one agonist of GHRH to a patient in need of treatment for diseases or disorders associated with growth hormone-releasing hormone (GHRH). Embodiments of the invention further comprise novel agonists of GHRH.

In one embodiment, a method of promoting survival of grafted cells or tissues in vivo comprising contacting the cells or tissues with or exposing the cells or tissues to an effective amount of GHRH and/or at least one agonist of growth hormone releasing hormone (GHRH). In preferred embodiments the grafted cells proliferate and repopulate damaged tissues in vivo. Preferably, the grafted cells and/or tissues comprise pancreatic cells and the grafted cells are islet cells.

In one embodiment, the agonist of GHRH comprises a peptide set forth as SEQ ID NO: 1 or SEQ ID NO: 2.

In another preferred embodiment, a method of preventing diabetes in a patient at risk of developing diabetes and/or treating a patient diagnosed with diabetes includes: obtaining or providing islet cells or tissues comprising islet cells; transplanting or grafting the islet cells and/or tissues including islet cells into a patient; administering a therapeutically effective amount of GHRH and/or at least one agonist of growth hormone releasing hormone (GHRH) to the patient. For example, the islet cells and/or tissues including islet cells or structures can be autologous, allogeneic, xenogeneic, syngeneic, or combinations of these.

In some embodiments, the islet cells and/or tissues comprising islet cells are contacted with or exposed to GHRH and/or at least one agonist of GHRH prior to transplantation into a patient.

In another preferred embodiment, the GHRH and/or at least one agonist of GHRH is administered pre-transplantation, concurrently with transplantation, post-transplantation or any combinations thereof.

In one preferred embodiment, a method of modulating insulin producing cell functions in vitro or in vivo includes: contacting an insulin producing cell or structure with or exposing an insulin producing cell or structure to an effective amount of GHRH and/or at least one agonist of growth hormone releasing hormone (GHRH). Preferably, the insulin producing cell comprises an islet cell or structure or a cell expressing a recombinant insulin molecule. For example, the cell expressing the recombinant insulin molecule can include a stem cell, pancreatic cell, transformed cell and/or cell sensitive to GHRH.

In an embodiment, a pharmaceutical composition comprises a therapeutically effective amount of growth hormone releasing hormone (GHRH) and/or an agonist of growth hormone releasing hormone (GHRH) for use in the treatment of a human or animal body.

An embodiment comprises exposing an insulin producing cell or structure to an effective amount of tesamorelin.

Other aspects are described infra.

DETAILED DESCRIPTION

Figure 1:
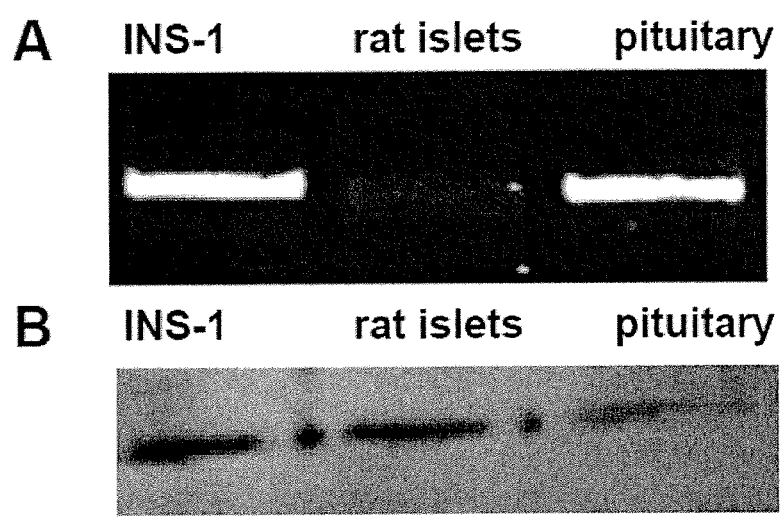
FIG. 1: The expression of GHRH-R based on mRNA levels (A) and receptor detection by western blots (B) was demonstrated in INS-1 cells and primary rat islets. Rat pituitary was used as a positive control.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

This application claims the benefit of U.S. Provisional Application No. 61/351,001, which is hereby incorporated by reference in its entirety.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Where particular values are described in the application and claims, unless otherwise stated the term "about" meaning within an acceptable error range for the particular value should be assumed.

As used herein, a "target cell" or "recipient cell" refers to an individual cell or cell which is desired to be, or has been, a recipient of agonists of growth hormone releasing hormone (GHRH). The term is also intended to include progeny of a single cell.

As used herein, "analog" of polypeptides refers to an amino acid sequence that is altered by one or more amino acid residues. The analog may have "conservative" changes, wherein a substituted amino acid has similar structural or chemical properties (e.g., replacement of leucine with isoleucine). More rarely, a analog may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

By the term "modulate," it is meant that any of the mentioned activities, are, e.g., increased, enhanced, increased, agonized (acts as an agonist), promoted, decreased, reduced, suppressed, blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" includes, but is not limited to, a mineral or organic acid salt of basic residues such as amines; an alkali or organic salt of acidic residues such as carboxylic acids. Preferably the salt is made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient", "individual", and "subject" are used interchangeably herein, and refers to a mammal to be treated, with humans being preferred. In some cases, the methods of the invention find use in experimental animals, in veterinary application, and in the development of animal models for disease, including, but not limited to, rodents including mice, rats, and hamsters; and primates.

"Treatment" or "therapeutic treatment" is an intervention performed with the intention of altering the pathology or symptoms of a disorder. "Treatment" may also be specified as palliative care. Accordingly, "treating" or "treatment" of a state, disorder or condition includes: (1) preventing or delaying the appearance of clinical symptoms of the state, disorder or condition developing in a human or other mammal that may be afflicted with the state, disorder or condition, but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

"Prevention" is an intervention performed with the intention of preventing the development of a disorder. "Prevention" refers to prophylactic or preventative measures. Those in need of prevention include those in which the disorder is to be prevented, for example, a human or other mammal that may be predisposed to the disorder. The benefit to an individual in which the disorder is to be prevented is either statistically significant or at least perceptible to the patient or to the physician.

Agonists of GHRH

Since 1922, insulin has been the only available therapy for the treatment of type 1 diabetes and other conditions related to lack of or diminished production of insulin. It is well established that at the onset of type 1 diabetes, patients have already lost at least 90% of their islets and their number of islets continues to steadily decline. However what has recently become clear is that not only in type 1 diabetes is there a deficit of islet mass, but also at the time of diagnosis of type 2 diabetes, patients exhibit a loss of at least 50% of the islet mass and number. As with type 1 patients, the number and mass of islets continues to decline in type 2 diabetes, not from autoimmune attack, but because the beta cells effectively become "burned out." Although this decline occurs more rapidly in type 1 patients, there is still a decline of 10-20% per year among type 2 patients.

A common misunderstanding is that insulin resistance causes type 2 diabetes. Although insulin resistance is a feature of both diabetes and obesity, diabetes does not occur as a result of insulin resistance without the coexistence of reduction of islet mass leading to reduction in insulin secretion. Diabetes occurs when there is a critical reduction in islet mass and function that prevents an adequate insulin response to a carbohydrate stimulus. Despite some regenerative ability of the beta cells within the islet structures, the islets have a much slower ability to regenerate. Even in the face of blocking the autoimmune destruction of the insulin-producing cells in the pancreas, without new methods of regenerating islets, there will not be an end to type 1 diabetes. Loss of islet mass is the basis of both type 1 and 2 diabetes, and more recent studies have demonstrated that prediabetes, insulin resistant states, hypertension, inactivity and family history are islet stressors associated with diminished islet mass.

Despite decades of research and the advent of pancreatic islet cell transplantation and newer claims of success resulting from the Edmonton Protocol for islet cell transplantation, the success has not been replicated in the United States. At four years post-transplant, fewer than 10% of patients who have received islet cell transplants remain insulin independent. Additionally, despite new immune suppression protocols, there is an 18% rate per patient of serious side effects.

In a normally functioning pancreas, small numbers of islets die naturally on a day-by-day basis and are replaced as required to keep glucose levels under control. On average, this regenerative process known as islet neogenesis replaces islets at a rate of approximately 2% per month. In nondiabetic patients, the beta cell mass within the existing islets can expand or contract depending on the insulin needs of the individual. This process, referred to as "beta cell proliferation", is not thought to occur in patients with type 1 diabetes and appears to be limited in type 2 patients.

Islets are formed in late embryogenesis, and pregnancy data demonstrates the islet population grows postnatally and islet neogenesis precedes beta cell expansion during fetal development in pregnancy. Furthermore, postnatally in humans, there are precursor cells within the pancreas that are capable of expansion, these occur naturally and efficiently differentiate into clusters of islets. The primary way in which patients with type 1 or later-stage type 2 diabetes manage their disease is by administering insulin, either via subcutaneous injection or by using a subcutaneous pump infusion. As well as the obvious lifestyle disadvantages, insulin therapy does not match the body's normal glucose control mechanisms and, therefore, does not fully manage glucose fluctuations. Even the best-controlled type 1 diabetic patients do not have anything remotely like a normal glucose metabolism.

Proof of the elasticity of the pancreas with respect to the generation of new pancreatic β cells throughout one's lifetime accompanied by pancreatic cell death or apoptosis has replaced the long held concept that the number of insulin producing islet cells is fixed at birth and sustained throughout life. It is currently accepted that pancreatic islet cell neogenesis occurs from progenitor cells that exist within the adult pancreas. Studies confirm that progenitor cells exist within both the islet and ductal and other fractions of the adult human pancreas, and that upon stimulation with HIP, there is both increased insulin production and islet numbers. This supports the data on pancreatic plasticity during pregnancy where, in studies among type 1 women, as many as ⅓ of women have a dramatic reduction in insulin requirements, with some women coming off insulin completely during their pregnancy. Even among patients who have had type 1 diabetes for decades, during pregnancy, many secrete normal levels of C-peptide, when C-peptide was non-detectable at the onset of pregnancy. Similarly, patients with type 1 diabetes having received renal transplants and on long term immunosuppression have been observed to regenerate insulin producing islets. The studies and types of agents to potentially arrest the destruction of islet cells have varied considerably. The types of agents include general immunosuppressant agents which have typically been used in organ transplants, specifically targeted antibodies to those lymphocytes which attack the islets, along with other agents such as Vitamin D, in which a deficiency has been associated with a higher incidence of diabetes.

Thus, therapeutic strategies for transplantation of pancreatic islet cells are urgently needed to expand β-cell mass by stimulating islet cell proliferation and/or prolonging islet cell survival. Control of the islets by different growth factors provides a potential venue for augmenting β-cell mass. Without wishing to be bound by theory, it is thought that GHRH promotes angiogenesis by increasing vascular endothelial growth factors (VEGF). VEGF and vascularization play a role in beta cell function and islet regeneration (21, 22). In the present study, described in detail in the examples section which follows, the GHRH receptor splice variant-1 (SV-1) (23, 24) was expressed in rat insulinoma INS-1 cells as well as in rat and human pancreatic islets. The effects of a synthetic GHRH agonist on beta cell survival and cell proliferation was examined both in vitro and in vivo. Briefly, in the in vitro studies of INS-1 cells, the GHRH agonist JI-36 caused a significant increase in cell proliferation and a reduction of cell apoptosis. JI-36 increased islet size and glucose-stimulated insulin secretion in isolated rat islets after 48-72 hrs. At the ultrastructural level, INS-1 cells treated with agonist JI-36 revealed a metabolic active stimulation state with increased cytoplasm. Co-incubation with the GHRH antagonist MIA-602 reversed the actions of the agonist JI-36, indicating their specificity. In vivo, the function of pancreatic islets was assessed by transplantation of rat islets under the kidney capsule of streptozotocin-induced diabetic NOD-SCID mice. Islets treated with GHRH agonist JI-36 were able to achieve normoglycemia earlier and more consistently than untreated islets. Furthermore, in contrast to diabetic animals transplanted with untreated islets, insulin response to an intraperitoneal glucose tolerance test (IPGTT) in animals receiving islets treated with agonist JI-36 was comparable to that of normal healthy mice. The results of the study herein, provides evidence that agonists of GHRH represent a promising pharmacological therapy aimed at promoting islet graft growth and proliferation in diabetic patients.

Thus, in a preferred embodiment, a method of promoting islet graft growth and proliferation of islets comprises administering a therapeutically effective dose of GHRH and/or an agonist of GHRH to a culture or patient. The islets can be pre-treated with GHRH and/or at least one agonist of GHRH, e.g. JI-36, prior to transplantation in the case of a patient. In other preferred embodiments, a therapeutically effective dose of GHRH and/or an agonist of GHRH is administered to a patient prior to the transplantation of cells or tissues. In another preferred embodiment, a therapeutically effective dose of GHRH and/or an agonist of GHRH is administered to a patient currently with the transplantation of cells or tissues. In another preferred embodiment, a therapeutically effective dose of GHRH and/or an agonist of GHRH is administered to a patient after transplantation or grafting of tissues or cells. In other preferred embodiments, the therapeutically effective amounts of GHRH and/or an agonist of GHRH are administered to patients at various time points, such as: pre-transplantation, concurrently with the transplantation of cells or tissues, post-transplantation or any combinations of timing and dosing thereof. The cells or tissues can be treated with one or more agonists of GHRH prior to transplantation or just prior to transplantation.

Agonist of GHRH means a compound other than GHRH which has the function of binding to and stimulating GHRH receptors, resulting in the release of growth hormone, or another physiological, endocrine or cellular response specific for GHRH. A GHRH agonist may comprise a full length GHRH sequence in which certain modifications have been made, e.g., amino acid residues have been substituted, side groups have been added, such as a hexenoyl moiety, or a salt has been formed, such as acetate salt, for example tesamorelin. Tesamorelin is the acetate salt of a sequence having a hexenoyl moiety attached to the N-terminal part of the GHRH amino acid sequence. The amino acid sequence of GHRH, starting at the N-terminal part is: $Tyr^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Lys^{12}$-$Val^{13}$-$Leu^{14}$-$Gly^{15}$-$Gln^{16}$-$Leu^{17}$-$Ser^{18}$-$Ala^{19}$-$Arg^{20}$-$Lys^{21}$-$Leu^{22}$-$Leu^{23}$-$Gln^{24}$-$Asp^{25}$-$Ile^{26}$-$Met^{27}$-$Ser^{28}$-$Arg^{29}$-$Gln^{30}$-$Gln^{31}$-$Gly^{32}$-$Glu^{33}$-$Ser^{34}$-$Asn^{35}$-$Gln^{36}$-$Glu^{37}$-$Arg^{38}$-$Gly^{39}$-$Ala^{40}$-$Arg^{41}$-$Ala^{42}$-$Arg^{43}$-$Leu^{44}$. A GHRH agonist may comprise a GHRH sequence to which amino acid deletions, insertions, and/or substitutions have been made. A GHRH agonist may also be a fragment or modified fragment of GHRH having the capability to bind to the GHRH receptor and stimulate release of growth hormone. The biological activity of GHRH is understood to reside in the N-terminal 1-29 amino acid sequence of this peptide (12). Thus, fragments or modified fragments between amino acid residues 1 and 29 are expected to be useful.

In another preferred embodiment, a method of preventing or treating diabetes in a patient, comprises administering to a patient a therapeutically effective amount of GHRH and/or at least one agonist of growth hormone releasing hormone (GHRH). The GHRH and/or agonist(s) can be administered over periods of time and the growth or long term survival of islet cells can be determined.

In another preferred embodiment, a method of preventing or treating diabetes in a patient comprises the grafting of cells or tissues, such as pancreatic islet cells, in a patient and administration of a therapeutically effective amount of GHRH and/or an agonist of GHRH.

In yet another preferred embodiment, a method of increasing the success of renal transplantation comprises administering to a patient a therapeutically effective amount of GHRH and/or an agonist of GHRH to a patient. The GHRH and/or agonist of GHRH can be administered with one or more other therapies including immunosuppressive therapies. The GHRH and/or agonist of GHRH promotes the survival of the grafted cell, tissues or organs.

In yet another preferred embodiment, a method of treating newly diagnosed or pre-existing diabetes mellitus in a patient, comprising administering to the patient GHRH and/or an agonist of GHRH that stimulates pancreatic islet cell regeneration and/or transformation of new insulin producing islets or islet cells. The agonist can be administered in combination with an agent that stimulates pancreatic islet cell regeneration and/or transformation of new insulin producing islets. An agent that stimulates pancreatic islet cell regeneration and/or transformation of new insulin producing islets includes, but is not limited to, Human proIslet Peptide (HIP), Optimized HIP, hamster INGAP other islet neogenesis agents. Preferably, the islet neogenesis agent is selected from HIP and Optimized HIP, preferably HIP2 and Optimized HIP2, such as HIP2B.

In another preferred embodiment, an immunosuppressive or immune tolerance agents can also be administered with the agonists of GHRH. Examples of agents include, but are not limited to, mycophenolate mofetil, daclizumab, rituximab (anti CD20), anti CD3 antibodies including hOKT3 gamma 1 (Ala-Ala), also known as MGA031 and the monoclonal antibody TRX4 (ChAglyCD3), CTLA4-Ig (abatacept) a selective costimulation modulator as it inhibits the costimulation of T cells, campath-1H, anti-CD52 antibody, a humanized monoclonal antibody to T-cells, polyclonal anti-T-lymphocyte globulin (ATG), DiaPep277, anti-GAD antibody vaccine based on the 65 kDa isoform of the recombinant human glutamic acid decarboxylase protein (rhGAD65), and diazoxide. Preferably, each agent is administered at a therapeutically effective amount.

The combination of therapies may restore more normal glucose metabolism, including achieving and maintaining appropriate levels of insulin, amylin, glucagon, somatostatin and pancreatic polypeptides that are normally secreted from islets among patients without diabetes. By restoring normal islet function, and protecting the newly form islets, there will, in turn, be improvement in preprandial and postprandial glucose levels, hemoglobin A1C, triglycerides, and glucagon and ameliorate the significant weight gain and increased risk for serious hypoglycemia that has been associated with tight glycemic control utilizing exogenous insulin among insulin-requiring patients, whether they have type 1 or type 2 diabetes.

In certain embodiments, the method may further comprise administering a beta cell or islet function optimizing agent. Such agents include, but are not limited to, Glucagon Like Peptide-1 (GLP-1) and its analogs; Gastric Inhibitory Peptide/Glucose-Dependent Insulinoptropic polypeptide (GIP), Amylin, and its analog, PRAMLINTIDE, and GLP-1 receptor agonists, such as LIRAGLUTIDE (NN2211) and Exendin-4/exenatide, or compounds which halt the destruction of GLP-1, such as Dipeptidyl Peptidase-4 inhibitors, (DPP-4 inhibitors), including but not limited to VILDAGLIPTIN, SITAGLIPTIN, SAXAGLIPTIN, and PHX1149. Other compounds which may improve existing islet function include: gastrin, epidermal growth factor-1 and insulin sensitizing agents including the thiazolidinediones, including but not limited to ROSIGLITAZONE and PIOGLITAZONE, AGI-1067, an anti-inflammatory antioxidant agent that works by inhibiting signaling pathways that are activated in response to oxidative stress and pro-inflammatory stimuli, RIMONABANT and other drugs that block, the cannabinoid receptor 1 (CB1), gut peptide, PYY, inclusive of, but not limited to PYY3-36 (PYY) nasal spray, the hypothalamic neuropeptide Y (NPY) and drugs that impact the leptin, ghrelin, pro-opiomelanocortin/melanocortin pathways or the melanocortin receptor, orlistat, which impacts the gut, centrally acting sibutramine, or acarbose, which delays carbohydrate absorption along the brush border of the intestine. The additional therapy may be beneficial, particularly in patients with type 1 diabetes who are above their ideal body weight and predisposed to peripheral insulin resistance.

In another preferred embodiment, a method of increasing the survival rate of transplanted cells in vivo, comprising administering to a patient GHRH and/or one or more GHRH agonists prior to transplantation, concurrently with transplantation, post transplantation, or combinations thereof. Preferably the transplanted cells are islet cells; however, any cell type can be used, depending on the condition or disorder to be treated.

In another preferred embodiment, the cells, such as for example, islet cells are pre-treated with GHRH and/or one or more GHRH agonists prior to transplantation in a patient. The cells can be allogeneic, xenogeneic, syngeneic, allogeneic, autologous or combinations thereof. In other embodiments the cells are stem cells.

In an embodiment, an insulin producing cell function is modulated in vitro and/or in vivo by exposing an insulin producing cell to an effective amount of GHRH and/or at least one agonist of growth hormone releasing hormone (GHRH). The insulin producing cell can be, for example, an islet cell and/or a cell expressing a recombinant insulin molecule. A cell expressing a recombinant insulin molecule can be a cell incorporating DNA modified by recombinant techniques that directs the cell to express insulin or an insulin derivative. For example, the incorporated DNA may induce a cell to express more insulin than it does in its native state, or may induce a cell that does not express insulin in its native state to express insulin. For example, the cell expressing the recombinant insulin molecule can include a stem cell, pancreatic cell, transformed cell, and/or cell sensitive to GHRH.

Nomenclature:

The nomenclature used to define the amino acid residues and synthetic peptides is that specified by the IUPAC-IUB Commission on Biochemical Nomenclature (*European J. Biochem.*, 1984, 138, 9-37). By natural amino acid is meant one of the common, naturally occurring amino acids found in proteins comprising Gly, Ala, Val, Leu, Ile, Ser, Thr, Lys, Arg, Asp, Asn, Glu, Gln, Cys, Met Phe, Tyr, Pro, Trp and His. By Nle is meant norleucine, by Abu is meant alpha amino butyric acid, by Orn is meant ornithine, and by Aib is meant alpha iso-butyric acid. Other abbreviations used are: Boc-(tert-butyloxycarbonyl-); 2-Br-Cbz (2-bromo-benzyloxycarbonyl-); (Cbz-benzyloxycarbonyl-); Chx- (cyclohexyl-); 2-Cl-Cbz- (2-chloro-benzyloxycarbonyl-); DCCl (dicyclohexylcarbodiimide); DIC (diisopropylcarbodiimide); DCM (dichloromethane); DIEA (diisopropylethylamine); DMF (dimethylformamide); HOBt (1-hydroxybenzotriazole); HPLC (high performance liquid chromatography); MeOH (methyl alcohol); TFA (trifluoroacetic acid); and Tos- (p-toluensulfonyl-).

The amino acid sequences of the synthetic peptides are numbered in correspondence with the amino acid residues in hGH-RH(1-29); thus, for example, the $Ala^4$ and $R^8$ in the synthetic peptides occupy the same position in the sequence as the $Ala^4$ and $R^8$ residues in hGH-RH(1-29).

The convention under which the N-terminal of a peptide is placed to the left, and the C-terminal to the right is also followed herein. It should be understood that the terms N- and C-terminal used with respect to the synthetic peptides mean $Q^1$-CO— and —NH-$Q^2$ respectively. Where applicable, standard three-letter abbreviations are used for coded amino acids. Noncoded amino acids and N-acyl moieties are abbreviated as follows: Abu, α-aminobutyric acid; Agm, agmatine; Dat, desaminotyrosine; Har, homoarginine; Nle, norleucine.

Examples of agonists of GHRH have been described; see, for example U.S. Pat. No. 5,792,747 which is incorporated by reference herein in its entirety. Examples of preferred agonists include synthetic peptides having the sequence set forth as SEQ ID NO: 1 (Formula I):

$Q^1$-CO-$R^2$-$R^3$-$Ala^4$-$Ile^5$-$Phe^6$-$Thr^7$-$R^8$-$Ser^9$-$Tyr^{11}$-$Arg^{11}$-$R^{12}$-$R^{13}$-$Leu^{14}$-$R^{15}$-$Gln^{16}$-$Leu^{17}$-$Ser^{18}$-$Ala^{19}$-$Arg^{20}$-$R^{21}$-$R^{22}$-$R^{23}$-$Gln^{24}$-$R^{25}$-$Ile^{26}$-$R^{27}$-$R^{28}$-NH-$Q^2$

Wherein $Q^1$ is an omega or alpha-omega substituted alkyl having the structure:

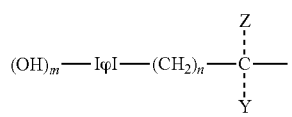

Wherein IφI is phenyl; Y is H, —$NH_2$, $CH_3CONH$— or $CH_3NH$—; Z is H or $CH_3$; m is 1 or 2 and n is 0, 1 or 2; $R^2$ is Ala, Abu or Aib; $R^3$ is Asp or Glu; $R^8$ is Asn, Ser, Gln or Thr; $R^{12}$ is Lys or Orn; $R^{13}$ is Val or Ile; $R^{15}$ is Ala, Gly or Abu; $R^{21}$ is Lys or Orn; $R^{22}$ is Leu, Ala or Abu; $R^{23}$ is Leu, Ala or Abu; $R^{25}$ is Asp or Glu; $R^{27}$ is Met, Nle, Ile, or Leu; $R^{28}$ is Asp, Asn or Ser; and, $Q^2$ is a lower omega-guanidino-alkyl group having a formula:

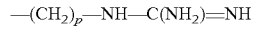

Wherein p is 2-6.

In another preferred embodiment, the synthetic peptides comprise the sequence set forth as SEQ ID NO: 2 (Formula II):

$Q^1$-CO-$Ala^2$-$Asp^3$-$Ala^4$-$Ile^5$-$Phe^6$-$Thr^7$-$R^8$-$Ser^9$-$Tyr^{10}$-$Arg^{11}$-$R^{12}$-$Val^{13}$-$Leu^{14}$-$R^{15}$-$Gln^{16}$-$Leu^{17}$-$Ser^{18}$-$Ala^{19}$-$Arg^{20}$-$R^{21}$-$Leu^{22}$-$Leu^{23}$-$Gln^{24}$-$Asp^{25}$-$Ile^{26}$-$R^{27}$-$R^{28}$-NH-$Q^2$ wherein $Q^1$, $R^8$, $R^{12}$, $R^{15}$, $R^{21}$, $R^{27}$, $R^{28}$ and $Q^2$ are as defined above. Preferably, $Q^1$-CO is Dat; $R^8$ is Asn, Ser, Gln or Thr; $R^{15}$ is Abu; at least one of $R^{12}$ and $R^{21}$ is Orn; $R^{27}$ is Met or Nle; $R^{28}$ is Ser or Asp; and NH-$Q^2$ is Agm. In certain preferred synthetic peptides of Formula II, $Q^1$-CO is Dat, $R^{15}$ is Abu; $R^{21}$ is Orn; $R^{27}$ is Nle; and NH-$Q^2$ forms Agm.

In one preferred agonist, in $Q^1$, m is 1, n is 1 and Y and Z are H, so that $Q^1$-CO forms Dat; $R^{12}$ is Orn, $R^{15}$ is Abu, $R^{21}$ is Orn, $R^{27}$ is Nle, $R^{28}$ is Ser; and in $Q^2$, p is 4, so that —NH-$Q^2$ forms Agm, the peptide has the formula: $Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Orn^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Ile^{26}$-$Nle^{27}$-$Ser^{28}$-NH—$(CH_2)_4$—NH—$C(NH_2)$=NH. This analog may be expressed under a well known convention as follows: ($Dat^1$, $Orn^{12,21}$, $Abu^{15}$, $Nle^{27}$, $Agm^{29}$)-hGH-RH(1-29).

In another preferred embodiment, an agonist of GHRH comprises a synthetic peptide wherein $Q^1$-CO— forms Dat, $R^{12}$ is Orn, $R^{15}$ is Abu, $R^{21}$ is Orn, $R^{27}$ is Nle, $R^{28}$ is Asp; and —NH-$Q^2$ forms Agm, the peptide has the formula: $Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Orn^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Ile^{26}$-$Nle^{27}$-$Asp^{28}$-NH—$(CH_2)_4$—NH—$C(NH_2)$=NH, which may be abbreviated as: ($Dat^1$, $Orn^{12,21}$, $Abu^{15}$, $Nle^{27}$, $Asp^{28}$, $Agm^{29}$)hGH-RH(1-29); this synthetic peptide is also termed JI-34.

In yet another preferred embodiment, an agonist of GHRH comprises a synthetic peptide wherein $Q^1$-CO forms Dat, $R^8$ is Thr, $R^{12}$ is Orn, $R^{15}$ is Abu, $R^{21}$ is Orn, $R^{27}$ is Nle, $R^{28}$ is Asp; and —NH-$Q^2$ forms Agm, the peptide has the formula: $Dat^1$-$Ala^2$-$Asp^3$-$Ala^4$-$Ile^5$-$Phe^6$-$Thr^7$-$Thr^8$-$Ser^9$-$Tyr^{10}$-$Arg^{11}$-$Orn^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Ile^{26}$-$Nle^{27}$-$Asp^{28}$-$NH(CH_2)$—NH—$C(NH_2)$=NH, which may be abbreviated as: ($Dat^1$, $Thr^8$, $Orn^{12,21}$, $Abu^{15}$, $Nle^{27}$, $Asp^{28}$, $Agm^{29}$)hGH-RH(1-29); this synthetic peptide is also termed JI-36.

Similarly, where $Q^1$-CO is Dat, $R^8$ is Gln, $R^{12}$ is Orn, $R^5$ is Abu, $R^{21}$ is Orn, $R^{27}$ is Nle, $R^{28}$ is Asp; and $Q^2$ forms Agm, the peptide has the formula: $Dat^1$-$Ala^2$-$Asp^3$-$Ala^4$-$Ile^5$-$Phe^6$-$Thr^7$-$Gln^8$-$Ser^9$-$Tyr^{10}$-$Arg^{11}$-$Orn^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Ile^{26}$-$Nle^{27}$-$Asp^{28}$-NH—$(CH_2)_4$—NH—$C(NH_2)$=NH, which may be abbreviated as: ($Dat^1$, $Gln^8$, $Orn^{12,21}$, $Abu^{15}$, $Nle^{27}$, $Asp^{28}$, $Agm^{29}$)hGH-RH(1-29); this synthetic peptide is also termed JI-38.

In another preferred embodiment, a method of promoting islet cell proliferation in a patient comprises administering to a patient one or more agonists of GHRH at one or more time points pre-transplantation of the cells, concurrently with transplantation of the cells, post-transplantation of the cells, or combinations thereof. The cells can also be pre-incubated or pre-treated with GHRH and/or an agonist of GHRH, or can be transplanted and the agonist administered concurrently to a patient.

Any one or more of the GHRH agonists can be administered with one or more other therapeutic agents. The combination of therapies can restore more normal glucose metabolism, including achieving and maintaining appropriate levels of insulin, amylin, glucagon, somatostatin and pancreatic polypeptides, which in turn will improve premeal and postprandial glucose levels, triglycerides, and glucagon and ameliorate the significant weight gain and increased risk for serious hypoglycemia that is associated with tight glycemic control occurring in patients with newly diagnosed and/or preexisting type 2 diabetes and those with prediabetes and impaired glucose tolerance.

In another embodiment of the present invention, provided are methods for treating conditions relating to aberrant glucose regulation or pathologies associated with impaired pancreatic function comprising administering GHRH and/or an agonist of GHRH. These agonists can be administered with one or more beta cell or islet function optimizing agents. Such conditions included, but not limited to, prediabetes, impaired glucose tolerance, insulin resistant syndromes, the metabolic syndrome, obesity, overweight, polycystic ovarian syndrome (PCOS), anovulatory cycles, fasting hyperlipidemia/hypercholesterolemia, elevated fasting total cholesterolemia, elevated LDL and VLDL cholesterol, family history of diabetes and some forms of impotence and sexual dysfunction associated with the metabolic syndrome, overweight obesity, insulin resistance or inactivity. The islet cell neogenesis agents include but not limited to Human proIslet Peptide (HIP), Optimized HIP, hamster INGAP or other agents that result in islet neogenesis. The islet cell neogenesis agent is preferably HIP or Optimized HIP, preferably HIP2 or Optimized HIP2, such as HIP2B. Beta cell or islet function optimizing agents are agents which optimize existing pancreatic islet function, including, but are not limited to: Glucagon Like Peptide-1 (GLP-1) and its analogs. Gastric Inhibitory Peptide/Glucose-Dependent Insulinoptropic polypeptide (GIP), Amylin, and its analog, Pramlintide, and GLP-1 receptor agonists, such as Liraglutide (NN2211) and Exendin-4/exenatide, or compounds which halt the destruction of GLP-1, such as Dipeptidyl Peptidase-4 Inhibitors, (DPP-4 inhibitors), including but not limited to Vildagliptin, Sitagliptin, Saxagliptin, and PHX1149, gastrin, epidermal growth factor-1 and insulin sensitizing agents including the biguanide, Metformin, and the thiazolidinediones, including but not limited to Rosiglitazone and Pioglitazone, AGI-1067, an anti-inflammatory antioxidant agent that works by inhibiting signaling pathways that are activated in response to oxidative stress and pro-inflammatory stimuli, Rimonabant and other drugs that block the cannabinoid receptor 1 (CB1), gut peptide, PYY, inclusive of, but not limited to PYY3-36 (PYY) nasal spray, the hypothalamic neuropeptide Y (NPY) and drugs that impact the leptin, ghrelin, pro-opiomelanocortin/melanocortin pathways or the melanocortin receptor, orlistat, sibutramine and acarbose. Preferably, the agents are administered in therapeutically effective levels.

In another preferred embodiment, a method of preventing or reducing early apoptosis/death of islet and beta cells, GHRH and/or an agonist of GHRH can be used alone or in combination with one or more of the following agents listed above, which can address the underlying pathophysiology of these conditions and improve or treat such conditions.

Additionally, based on the patient's underlying medical issue, another agent may selected. For example, if the primary issue is overweight, pramlintide or GLP-1 or a GLP-1 analog may be selected for usage concomitantly with the islet neogenesis agent.

Further embodiments of the present invention provides methods for one or more agonists of GHRH that stimulate or optimize pancreatic islet cell growth, survival, proliferation, regeneration and/or transformation of new insulin producing cells or targets to treat conditions often relating to aberrant glucose regulation or pathologies associated with impaired pancreatic function including but not limited to prediabetes, impaired glucose tolerance, insulin resistant syndromes, the metabolic syndrome, obesity, overweight, polycystic ovarian syndrome (PCOS), anovulatory cycles, fasting hyperlipidemia/hypercholesterolemia, elevated fasting total cholesterol, elevated LDL and VLDL cholesterol, family history of diabetes and some forms of impotence and sexual dysfunction associated with the metabolic syndrome, overweight obesity, insulin resistance or inactivity.

Embodiments of the invention can even render some patients completely free of their dependence on administered insulin. When new islets are formed, not only are insulin and amylin replaced, which are secreted from the beta cells, but all four cell types within the islet are regenerated. Thus, diminished hormones other than insulin are replaced, and islet regeneration can significantly diminish or abolish insulin requirements in type 1 patients with significantly improved glucose control. By providing increased survival rates of transplanted islet cells the methods of the present invention have even greater promise, because they result in the sustained endogenous production of insulin resulting in improved, regulation of numerous glucoregulatory feedback mechanisms both with the islet to the alpha cells regulating glucagon and central receptors affecting glucose regulation in the brain.

Embodiments of the present invention treat the underlying pathologic mechanisms of type 1 diabetes, type 2 diabetes and conditions resulting from decreased insulin production due to an imbalance between destruction, regeneration, and sustenance of insulin producing islet cells. The methods and compounds of the invention can reduce the insulin requirements of patients currently taking the drug due to having type 1 or type 2 diabetes or another disease or condition of impaired glucose metabolism and/or insulin resistance creating abnormal physiology. Embodiments of the present invention can improve glucose control in such patients. In some patients, treatment in accordance with the methods of the invention can ameliorate or obviate the need for administered insulin.

Embodiments of the present invention can be used to treat any mammal, including humans and animals, suffering from a disease, symptom, or condition related to a diminished production of insulin due to the loss of pancreatic islet cells. Such diseases and conditions include, of course, type 1 diabetes mellitus, pre-type 1 diabetes, including but not limited to pre-diabetes in a type 1 patient as manifested by antibodies (anti-GAD65 and others) specific for type 1 diabetes, and latent autoimmune diabetes of adulthood (LADA). Moreover, the present invention can be practiced with therapeutic benefit for patients newly diagnosed as having type 1 diabetes, the siblings and first degree relatives of patients with type 1 diabetes, and people with positive antibodies indicative of future development of type 1 diabetes and/or other autoimmune conditions that indicate a predilection to type 1 diabetes.

The agonists and related methods and compositions can also be employed as adjunctive therapy to insulin therapy in type 1 diabetes in children and adults, to ameliorate glucose swings among patients with diabetes, and in patients with poorly controlled diabetes, hypoglycemic unawareness, and recurrent hypoglycemia in type 1 diabetes. The agonists and related methods and compositions of the invention can also be used to treat patients having recurrent pancreatitis or pancreatic cancer or another disorder or disease of the pancreas and can be used in all modalities of a need for auto islet regeneration/regeneration of one's own islets.

Administration

The agonists of GHRH useful in the methods of the invention can be administered by a variety of routes and using pharmaceutical formulations previously developed for other indications. Such delivery routes include, but are not limited to, at least for most known agents, inhalation, topical delivery, including micelle and nanosphere topical delivery systems, subcutaneous delivery including pump-assisted continuous infusion and disposable micro-pump, micro-needles and buccal delivery.

The particular route of administration and pharmaceutical formulation of an agonist used in the practice of the methods of the invention will be selected by the practitioner based on a patient's disease or condition being treated and the agent employed. A wide variety of pharmaceutical compositions can be employed in the methods of the invention. In some embodiments, extended use preparations can be used for ease of administration and increased efficacy.

Effective Amounts:

The compositions described above are preferably administered to a subject in an effective amount. A therapeutically effective amount is an amount which is capable of producing a desirable result in a treated animal or cell. As is well known in the medical and veterinary arts, dosage for any one animal depends on many factors, including the particular animal's size, body surface area, age, the particular composition to be administered, time and route of administration, general health, and other drugs being administered concurrently. An effective amount for use with a cell in culture will also vary, but can be readily determined empirically (for example, by adding varying concentrations to the cell and selecting the concentration that best produces the desired result). It is expected that an appropriate concentration would be in the range of about 0.001-50 µM. For example, an effective amount for use with a cell in culture and/or a therapeutically effective amount of GHRH and/or an agonist of growth hormone releasing hormone (GHRH) can be in the range of from about 0.001 µM, 0.01 µM, 0.1 µM, 1 µM, or 10 µM to about 0.01 µM, 0.1 µM, 1 µM, 10 µM, or 50 µM. For example, an effective amount for use with a cell in culture and/or a therapeutically effective amount of GHRH and/or an agonist of growth hormone releasing hormone (GHRH) can be about 1 µM.

Formulations:

A compound of the present invention can be formulated as a pharmaceutical composition. Such a composition can then be administered parenterally, by inhalation spray, rectally, or topically by other means in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, inhalation or infusion techniques.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

The methods and combinations of the present invention provide one or more benefits. Combinations of the present invention may allow for a lower dose of each agent. A benefit of lowering the dose of the compounds, compositions, agents and therapies of the present invention administered to a mammal includes a decrease in the incidence of adverse effects associated with higher dosages.

By lowering the incidence of adverse effects, an improvement in the quality of life of a patient undergoing treatment is contemplated. Further benefits of lowering the incidence of adverse effects include an improvement in patient compliance, a reduction in the number of clinical visits needed for the treatment of adverse effects, and a reduction in the administration of analgesic agents needed to treat pain associated with the adverse effects.

Alternatively, the methods and combination of the present invention can also maximize the therapeutic effect at higher doses.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition of the invention can be administered to a patient either alone, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition (see, e.g., Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncologic or other disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Formulations, techniques for formulation, routes of administration, and administration are known in the art, and are described, for example, in Remington's Pharmaceutical Sciences, 18$^{th}$ ed., Mack Publishing Co., Easton, Pa. (1990). Suitable routes may include rectal, transdermal, vaginal, transmucosal, and/or intestinal administration; parenteral delivery, including intramuscular, subcutaneous, intramedullary injections, as well as intrathecal, direct intraventricular, intravenous, intraperitoneal, intranasal, and/or intraocular injections, just to name a few.

The compositions described above may be administered to a subject in any suitable formulation. In addition to treatment topical formulations of the composition, the composition can be delivered by other methods. For example, the composition can be formulated for parenteral delivery, e.g., for subcutaneous, intravenous, intramuscular, and/or intratumoral injection. Other methods of delivery, for example, liposomal delivery and/or diffusion from a device impregnated with the composition might be used. The compositions may be administered in a single bolus, multiple injections, and/or by continuous infusion (for example, intravenously and/or by peritoneal dialysis). For parenteral administration, the compositions are preferably formulated in a sterilized pyrogen-free form. Compositions of the invention can also be administered in vitro to a cell (for example, to induce apoptosis in a cancer cell in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, and/or intestinal administration; parenteral delivery, including intramuscular, subcutaneous, intramedullary injections, as well as intrathecal, direct intraventricular, intravenous, intraperitoneal, intranasal, and/or intraocular injections, just to name a few.

For injection, the agents of the invention may be formulated in aqueous solutions, preferably in physiologically compatible buffers such as Hanks's solution, Ringer's solution, and/or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to the liposomal hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations, which can be used pharmaceutically. The preparations formulated for oral administration may be in the form of tablets, dragees, capsules, and/or solutions. The pharmaceutical compositions of the present invention may be manufactured in a manner that is itself known, e.g., by means of conventional mixing, dissolving, granulating, dragee-making, levitating, emulsifying, encapsulating, entrapping and/or lyophilizing processes.

Formulations suitable for topical administration include liquid or semi-liquid preparations suitable for penetration through the skin to the site of where treatment is required, such as liniments, lotions, creams, ointments and/or pastes, and drops suitable for administration to the eye, ear, and/or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogel. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, and/or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, and/or alginic acid and/or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and/or suitable organic solvents or solvent mixtures. Dyestuffs or pigments may be added to the tablets or dragee coatings for identification or to characterize different combinations of active compound doses.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. For example, the final pH value is one not irritating to human skin and preferably such that transdermal transport of the active compound, for example, GHRH and/or an agonist of growth hormone releasing hormone (GHRH), sulindac, peroxide, and/or arsenic trioxide, is facilitated. Without violating this constraint, the pH may be selected to improve the compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of the composition. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

Embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Survival and Proliferation of Pancreatic Islets

Materials and Methods
Peptide Analogues Preparation.
GHRH agonist JI-36 and GHRH antagonist MIA-602 were synthesized as previously described (17, 19, 20).
Rat Insulinoma Cell Line.
Rat insulinoma cells (INS-1) were cultured in RPMI 1640 medium (PAA, Pasching, Austria) supplemented with 2 mM L-glutamine, 10% fetal bovine serum (FBS), 1 mM Na-pyruvate, 50 µM 2-mercaptoethanol and 100 U/ml penicillin-streptomycin (Gibco, Gaithersburg Md.) in a humidified 5% $CO_2$/95% $O_2$ atmosphere at 37° C. The culture medium was changed every other day. Cells were grown for 72 hrs prior to experimentation. GHRH agonist JI-36 ($10^{-6}$-$10^{-9}$ M) and GHRH antagonist MIA-602 ($10^6$-$10^{-7}$ M) were used for 24-96 hrs, respectively.
Isolation of Rat Pancreatic Islets.
Pancreatic islets were isolated from male Wistar rats according to guidelines established by the University of Dresden Institutional Animal Care and Use Committee. Animals were anesthetized by 3% isoflurane; digestion solution (Collagenase V, Sigma-Aldrich, St. Louis, Mo.) was injected in situ via the pancreatic common bile duct. Islets were purified by centrifugation on a discontinuous Ficoll gradient (Mediatech). Purified islets were maintained in culture media (CMRL 1066, Mediatech, USA) supplemented with 10% FBS at 37° C. in a 5% $CO_2$ incubator. Volume and purity were determined by microscopic sizing after staining with dithizone (Sigma-Aldrich, St. Louis, Mo.).
Isolation of Human Pancreatic Islets.
Human pancreata from cadaver donors were obtained through Eurotransplant following consent for research use obtained from the next of kin and authorization by the German Foundation for Organ Transplantation. Islets were isolated using a modification of the automated Ricordi method (31). Briefly, collagenase NB1, neutral protease (Serva Electrophoresis, Heidelberg, Germany), and DNAse (Roche, Indianapolis, Ind.) were infused into the main pancreatic duct. Islets were separated from exocrine tissue by centrifugation on a continuous-density Biocoll gradient (Biochrom AG, Berlin, Germany) in a COBE 2991 cell processor (Lakewood, Colo.). For determination of purity and islet yield, islet samples were stained with dithizone (Sigma-Aldrich Corp., St. Louis, Mo.) and sized using an eyepiece reticle and inverted microscope. Islets were cultured in CMRL 1066 (Mediatech, Herndon, Va.) containing 2.5% human serum albumin at 37° C. in a 5% $CO_2$ incubator prior to experimentation.

Islet Equivalent Determination.
Triplicate samples of 100 to 300 islet particles were stained with dithizone (Sigma-Aldrich, St. Louis, Mo.), which binds zinc ions present specifically in islet β-cells, and sized using an eyepiece reticle and inverted microscope (32). The term islet particle describes an individual islet independent of its size. All islet particles with a diameter >50 µm were divided into classes of 50 µm increments (i.e., 50-100, 100-150, 150-200, etc.) for calculation of islet equivalents (IEQ). Each diameter class was converted into the mean volume of 150-µm diameter islets by a relative conversion factor. These factors allow converting the total islet particle number from any preparation into IEQ.
Exposure of INS-1 Cells, Rat and Human Islets to GHRH Analogues.
INS-1 cells were grown for 72 hrs prior to experimentation; islets were collected immediately after the isolation procedure and each were divided into three treatment groups: (1) Culture media with vehicle (DMSO) served as control group, (2) Culture media containing GHRH agonist JI-36 ($10^{-6}$ M), (3) culture media with JI-36 plus GHRH antagonist MIA-602 ($10^{-6}$ M). Media change and addition of the analogues was performed after 24 hrs and 48 hrs in islet cultures and every other day in INS-1 cell cultures.
Fluorescein Diacetate-Propidium Iodide Viability Staining.
Small aliquots of islets were transferred in phosphate-buffered saline (PBS) containing Petri dishes. Fluorescein diacetate (FDA) and propidium iodide (PI) were added to the samples at a final concentration of 0.5 and 75 µM, respectively. Using a fluorescence microscope, 100 islets were assessed for cell viability by estimating the percentage of viable cells (green) versus percentage of non-viable cells (red) within each islet. The percentage of viable cells was then calculated (33).
Measurement of Insulin Secretion by Static Challenge with Glucose.
For static insulin secretion in response to glucose challenge, islets were transferred into Petri dishes containing oxygenated Krebs-Ringer bicarbonate buffer (KRB, 137 mM NaCl, 4.7 mM KCl, 1.2 mM $KH_2PO_4$, 1.2 mM $MgSO_4$-$7H_2O$, 2.5 mM $CaCl_2$-$2H_2O$, 25 mM $NaHCO_3$, 0.25% BSA) and pre-incubated in 3.3 mM glucose at 37° C. (5% $CO_2$) for 30 min. Groups of 8-10 islets from the equilibration cultures were transferred to fresh oxygen-saturated media containing either 3.3 or 16.7 mM glucose and then incubated an additional 60 min in a 37° C. water bath with gentle shaking. Secreted insulin in the media was measured by ELISA (Millipore, Billerica, Mass.) and values normalized to extracted islet DNA (Quant-iT™ Picogreen, Invitrogen).
In Vivo Islet Functional Assessment.
NOD-SCID mice (MTZ breed) with induced diabetes were used as islet recipients following guidelines established by the University of Dresden Institutional Animal Care and Use Committee. Diabetes was induced by a single intraperitoneal injection of 180 mg/kg streptozotocin (Sigma-Aldrich, St. Louis, Mo.). Serum glucose was then measured daily using an Ascensia Elite glucometer (Bayer, Burr Ridge, Ill.). Mice were considered diabetic if non-fasting blood glucose (BG) was >350 mg/dL for two or more consecutive days. Rat islet preparations were used for transplantation. Islets from each preparation were divided into two groups, and JI-36 ($10^{-6}$ M) or vehicle (DMSO) was added to the culture media. Islets were cultured for 48 hrs prior to transplantation. After culture, samples of 300 IEQ were washed in transplant media (Ringer acetate with 5% glucose and 10% FBS), and transplanted to beneath the left kidney capsule. The animal experiments and housing were in accordance with institutional guidelines and German animal regulations.

Post-Transplant Follow Up.

The mice were observed for 30 days following transplantation. The non-fasting blood glucose levels were measured daily during the first week and twice a week thereafter. On day 25, mice were subjected to an intraperitoneal glucose tolerance test (IPGTT). Two days later, grafts were removed. This led to a recurrence of the diabetic state. This proves that restoration and maintenance of normoglycemia was due to islet graft function.

Definition of Metabolic Control.

On follow-up, sustained non-fasting blood glucose levels of ≤10 mM (≤180 mg/dl) were defined as "cure", 10 to 18 mM (180 to 320 mg/dl) as "partial function" of transplanted islets, and levels above 18 mM (>320 mg/dl) as "graft failure".

Intraperitoneal Glucose Tolerance Test.

Mice were fasted overnight (at least 6 hrs) before examination. A glucose solution was given at 3 g/kg BW i.p. and blood glucose was recorded before injection and 15, 30, 45, 60, 90 and 120 min following glucose injection. Non-transplanted mice were used as controls and tested concurrently.

Figure 2:
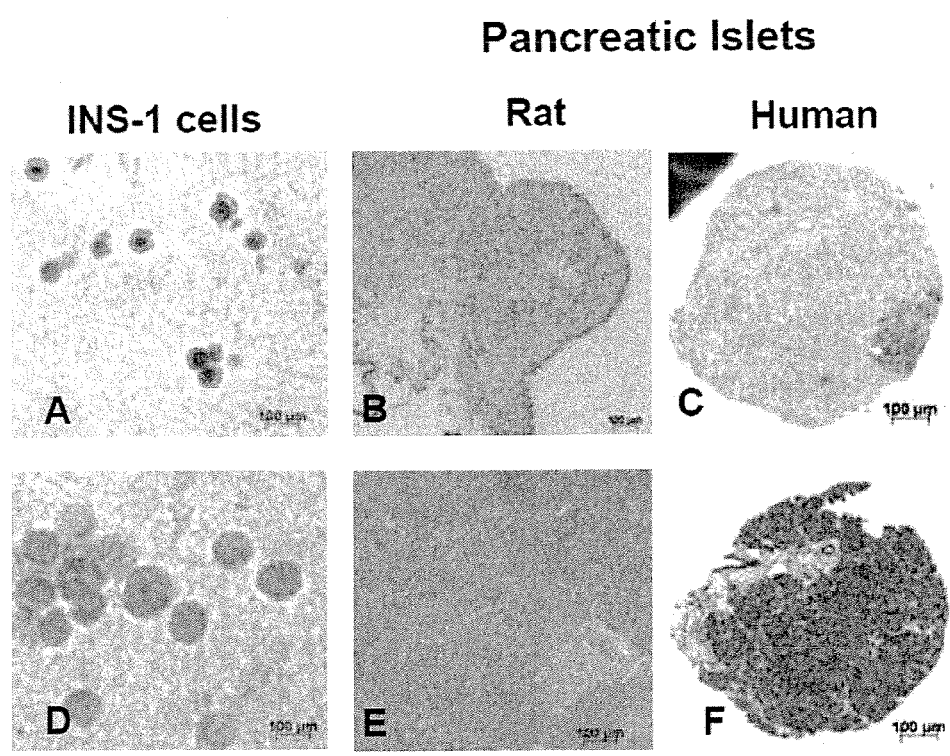
FIG. 2: Immunohistochemical staining of GHRH-R in INS-1 cells (A, D), rat islets (B, E) and human pancreatic islets (C, F). To demonstrate the presence of GHRH-R protein on islet beta-cells, co-staining with insulin was performed (F).

Growth Hormone-Releasing Hormone and its Agonistic Analogs:

These are shown in Table 1 below:

Immunohistochemical analysis showed pronounced GHRH-R immunostaining of INS-1 cells (FIGS. 2A, 2D), rat (FIGS. 2B, 2E) and human (FIGS. 2C, 2F) islets. To confirm the localization of GHRH-R on beta-cells, co-staining for insulin was performed (FIG. 2F).

Ultrastructural Analysis of Insulinoma Cells Before and after Incubation with the GHRH Agonist.

Figure 3:
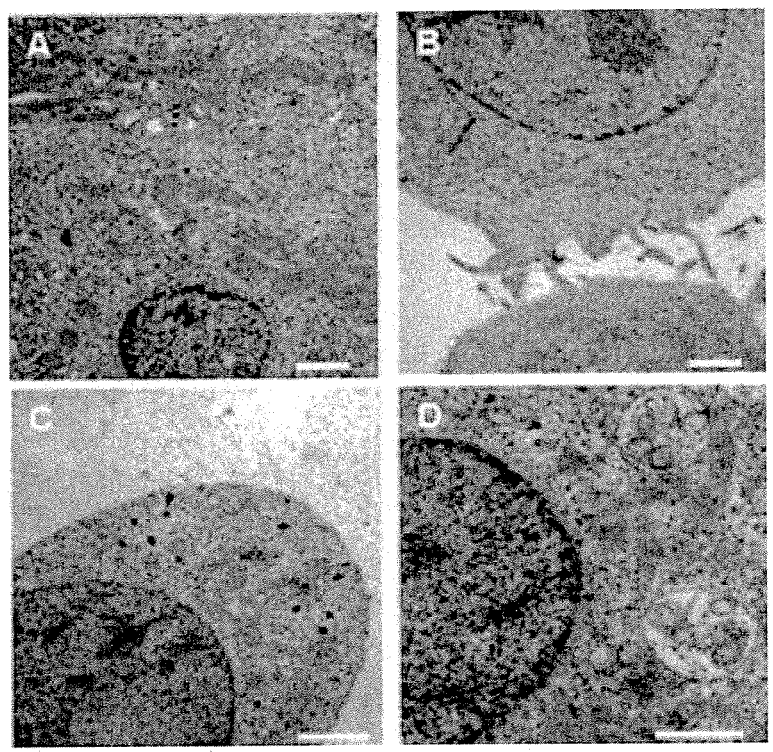
FIG. 3: Ultrastructural analysis of INS-1 cells. These cells under normal culture conditions demonstrate secretory granules frequently lining up at the cell membrane as well as a substantial number of cell membrane protrusions and filopodia (A, B). In contrast, islet cells treated with GHRH agonist JI-36 ($10^{-6}$ M) reveal an enlargement of the cell membrane and disappearance of filopodia. Furthermore, hyperplasia and enlargement of mitochondria as well as a conspicuous inclusion of vesicles into lysosomes could be found. In addition, an increasing amount of heterochromatin and nucleoli in the cell nucleus was also documented. These signs demonstrate a more active metabolic state of the islet cells (C, D). (scale bar in white=1 μm).

INS-1 cells under normal culture conditions were characterized by secretory granules close to the cell membrane (FIG. 3A). The cell surface itself extended long filopodia and other membrane protrusions (FIG. 3B). Treatment of islet cells with $10^{-6}$ M JI-36 produced an enlargement of the cell membrane and the volume of the cytoplasm. This was accompanied by the disappearance of membrane protrusions (FIG. 3C). Furthermore, mitochondria and lysosomes were also enlarged; the latter contained numerous vesicles, indicating intracytoplasmatic digestion of the contents (peptides, proteins) of secretory vacuoles, after the vacuoles fuse with lysosomes. Additional changes became obvious in the cell nucleus, demonstrating an increased amount of heterochromatin as well as nucleoli (FIG. 3D). These morphological changes demonstrate an increased active metabolic state of the islet cells.

Cell Proliferation Studies on Insulinoma Cells.

Incubation of INS-1 cells with JI-36 ($10^{-6}$-$10^{-9}$ M) for 24-96 hrs caused a significant and dose-dependent increase in

TABLE 1

Growth Hormone-Releasing Hormone GHRH(1-29)NH$_2$ and its agonistic analogs

| Amino acid residue | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| hGHRH (1-29)NH$_2$H— | Tyr | Ala | Asp | Ala | Ile | Phe | Thr | Asn | Ser | Tyr | Arg | Lys | Val | Leu | Gly | Gln |
| | 1 | | | | | | | 8 | | | | 12 | | | 15 | |
| hGH-RH | Tyr | | | | | | | Asn | | | | Lys | | | Gly | |
| JI-34 | Dat | | | | | | | — | | | | Orn | | | Abu | |
| JI-36 | Dat | | | | | | | Thr | | | | Orn | | | Abu | |
| JI-38 | Dat | | | | | | | Gln | | | | Orn | | | Abu | |

| Amino acid residue | 17 | 18 | 19 | 20 | 21 | 22 | 23 | 24 | 25 | 26 | 27 | 28 | 29 |
|---|---|---|---|---|---|---|---|---|---|---|---|---|---|
| hGHRH (1-29)NH$_2$H— | Leu | Ser | Ala | Arg | Lys | Leu | Leu | Gln | Asp | Ile | Met | Ser | Arg-NH$_2$ |
| | | | | | 21 | | | | | | 27 | 28 | 29 |
| hGH-RH | | | | | Lys | | | | | | Met | Ser | Arg-NH$_2$ |
| JI-34 | | | | | Orn | | | | | | Nle | Asp | Agm |
| JI-36 | | | | | Orn | | | | | | Nle | Asp | Agm |
| JI-38 | | | | | Orn | | | | | | Nle | Asp | Agm |

Non-coded amino acids are abbreviated as follows:
Dat: desaminotyrosine
Orn: ornithine
Abu: aminobutyric acid
Nle: norleucine
Agm: agmatine Results Expression of Receptor for GHRH in Insulinoma Cells and in Rat Islet Cells.

RT-PCR analysis demonstrated expression of GHRH-receptor (564 bp) in INS-1 cells and in rat islets. Rat pituitary was used as a positive control (FIG. 1A). In addition, the protein of the biologically more active splice variant SV-1 of GHRH-receptor was detected in INS-1 and rat islets by Western blotting (39.5 kDa). Rat pituitary was used as a positive control (FIG. 1B).

Figure 4:
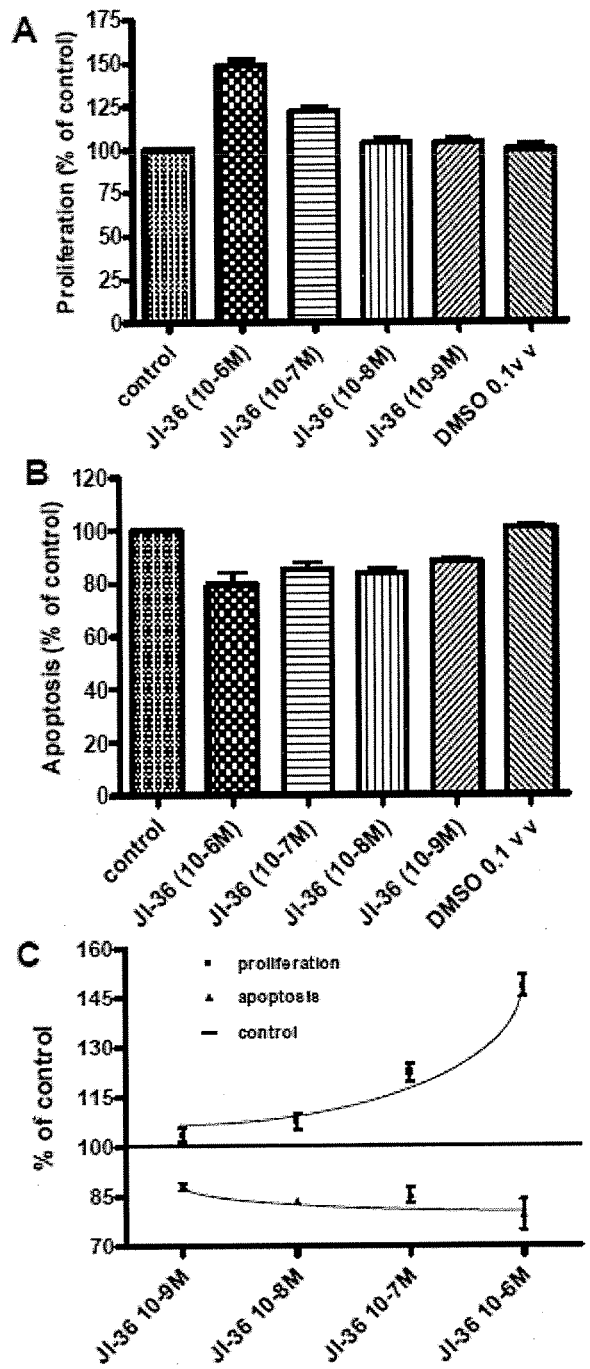
FIG. 4: In vitro effects of GHRH agonist JI-36 on INS-1 cells. (A) JI-36 ($10^{-6}$ M) stimulated cell proliferation significantly (50% increase compared to control) after 72 hrs in culture (n=3). (B) Apoptosis as indicated by activity of caspases 3 and 7 was significantly reduced by 20% after treatment with JI-36 ($10^{-6}$ M) for 72 hrs (n=3). (C) JI-36 treatment dose-dependently increased cell proliferation and conversely decreased the rate of apoptosis in INS-1 cells with the maximum effect at $10^{-6}$ M. * $p<0.001$;  $p<0.01$; * $p<0.05$.

Immunohistochemical Confirmation of the Expression of GHRH-Receptor Protein in Insulinoma Cells, Rat and Human Islets.

cell proliferation rates. The most effective concentration of the agonist was $10^{-6}$ M with a 50% increase after 72 hrs (FIGS. 4A, 4C). Co-incubation of INS-1 cells with the GHRH-agonist JI-36 ($10^{-6}$ M) and the GHRH-antagonist MIA-602 ($10^{-6}$ M) for 72 hrs reversed the proliferation-stimulating effect of the agonist.

Cell Apoptosis Studies on Insulinoma Cells.

Incubation of INS-1 cells with JI-36 ($10^{-6}$-$10^{-9}$ M) for 24-96 hrs resulted in a significant decrease in degree of cell apoptosis as measured by the reduction of activity of caspases 3 and 7. The maximal anti-apoptotic effect was seen after 72 hrs; the most effective concentration of the agonist causing this effect was $10^{-6}$ M (FIGS. 4B, 4C).

Determination of Islet Particle Number and Islet Size.

Figure 5:
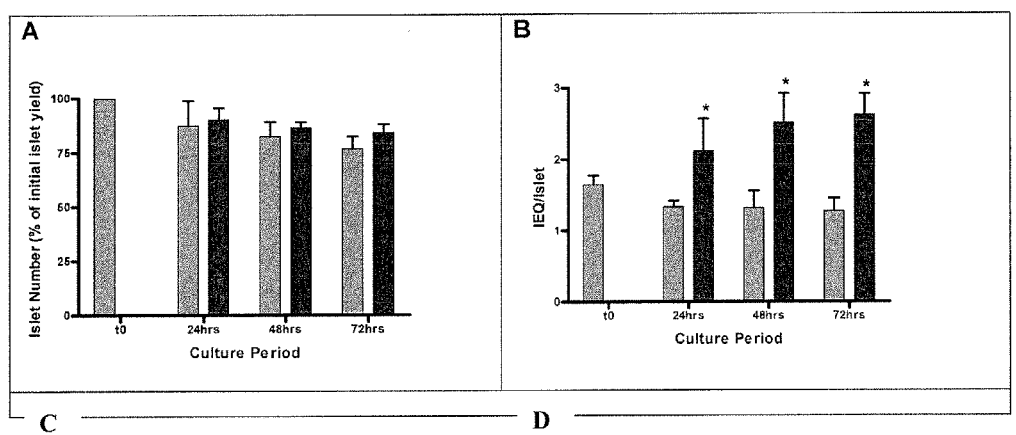
FIG. 5. Effect of JI-36 on islet number and islet size in vitro (n=4). (A) The number of islets decreased slightly over time in culture with no difference between treatment group and control. The bars represent the percentage of islet number compared to islet yield right after isolation (t0). (B) When converted to islet equivalents (IEQ), a significant difference between JI-36 treated islets and controls was seen after 24 hrs and continued to increase over time. Grey bars represent control group (n=4), black bars represent JI-36 treated islets (n=4); *$p<0.05$. (C, D) Immunostaining of islet serial sections for insulin (C, brown staining) and Ki-67 (D, brown staining) showed co-localization (arrowheads) of the proliferation marker within beta cells.

Cultures of isolated rat islets in the presence of JI-36 showed no relevant change in number of islet particles (IP) over time compared to control islets (FIG. 5A). Calculation of islet equivalents (IEQ) by relative conversion into islets of 150-μm diameter showed a significant change in IEQ/IP ratio, indicating a relative "islet growth" after 48 hrs, and up to 72 hrs, following exposure to JI-36 (FIG. 5B).

Immunohistochemical staining of the islets, after 72 hrs in culture with JI-36, for insulin and the proliferation marker Ki-67, showed co-localization of the two markers, indicating an induced proliferation, specifically although not exclusively in beta-cells (FIGS. 5C, 5D).

Measurement of Islet Membrane Integrity.

Rat islets were evaluated by fluorescent microscopy using FDA/PI staining. No difference in islet viability was observed between the groups after 24, 48 and 72 hrs in culture (72 hrs-time point: 93±2.2% for control islets, 96±3.3% for islets exposed to JI-36; n=4). Morphological appearance following dithizone staining also did not differ between treatment groups.

Effects of JI-36 on Glucose Stimulated Insulin Secretion.

Figure 6:
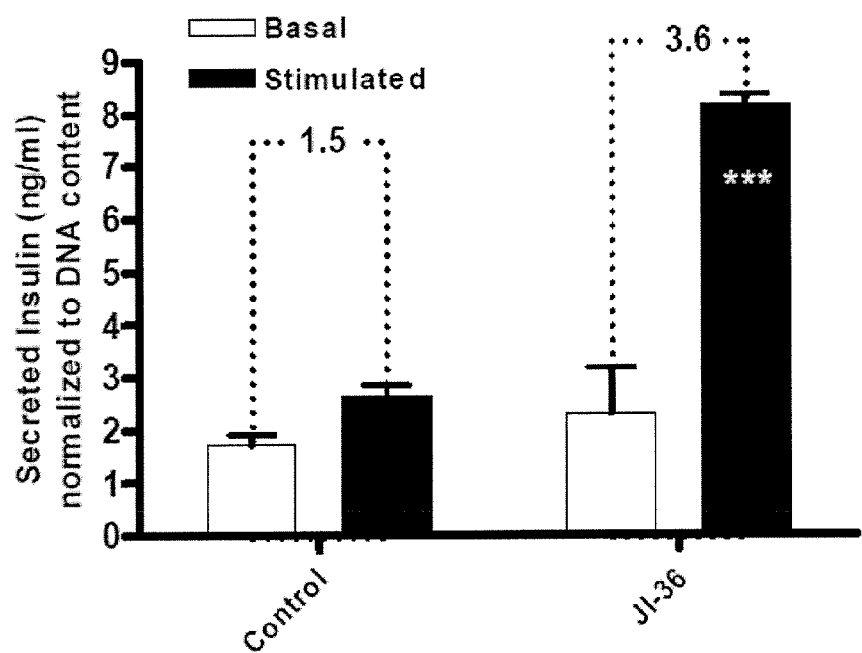
FIG. 6. Effect of GHRH agonist JI-36 on glucose stimulated insulin secretion. After equilibration at 3.3 mM glucose, islets were stimulated with high glucose concentration of 16.7 mM for 1 hour. Exposure to JI-36 did not cause a relevant difference in insulin secretion at basal conditions. Glucose challenge resulted in a significantly increased insulin release 3.6 fold relative to insulin release at basal glucose concentration when compared to untreated islets that increased insulin release 1.5 fold relative to insulin release at basal glucose concentration (n=5). Overall, pretreatment with JI-36 resulted in a more than double insulin release upon glucose stimulation compared to control (*** $p<0.001$).

In a static model of glucose-stimulated insulin secretion, exposure to JI-36 for 48 hrs resulted in a slight increase of insulin release into the culture media after 1 hr at basal (3.3 mM) glucose concentration as compared to control (2.3±0.5 ng/ml vs. 1.7±0.1 ng/ml; n=5). Upon stimulation with high levels of glucose (16.7 mM), insulin release from treated islets was significantly increased (3.6-fold) relative to insulin release at basal glucose concentration, while untreated islets augmented insulin release only 1.5-fold (8.2±0.2 ng/ml compared to control 2.6±0.2 ng/ml; n=5; $p<0.001$; FIG. 6). Thus, treatment of rat islets in vitro more than doubled total insulin release upon stimulation.

Performance of Islets Exposed to JI-36 In Vivo.

Figure 7:
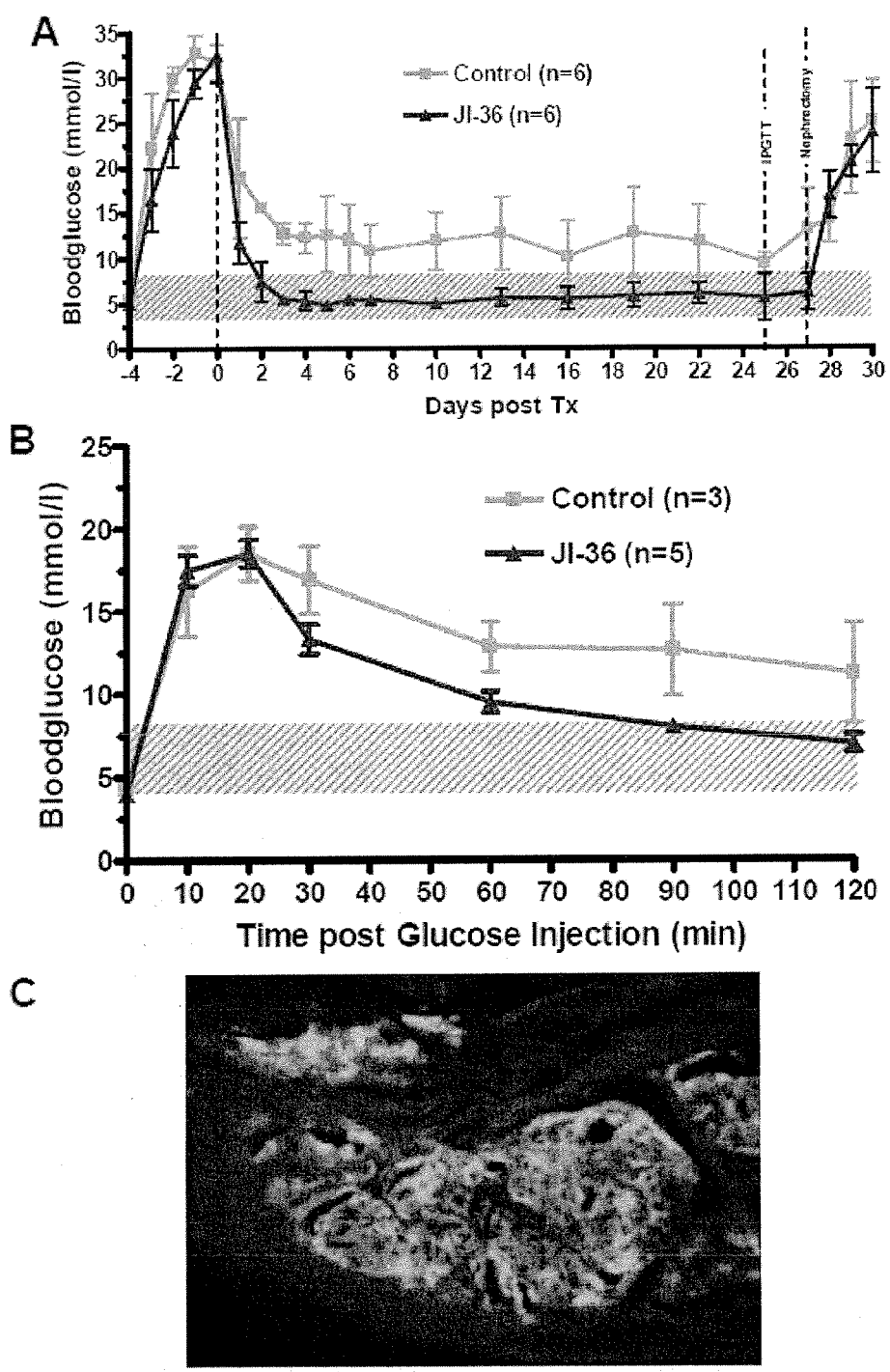
FIG. 7: Islet transplantation (300 Islet Equivalents) beneath the kidney capsule of streptozotocin-induced diabetic NOD-SCID mice. (A) After transplantation the control group showed a delayed decrease in blood glucose levels and only 3 out of 6 animals showed stable normoglycemia during the follow up period. Animals receiving a graft of islets pretreated with JI-36 showed rapid and persistent recovery from diabetes (5 out of 6 animals). (B) On day 25 following islet transplantation animals with normal glucose control were subjected to an intraperitoneal glucose tolerance test. While control animals responded in a delayed and insufficient manner to the glucose challenge, the group treated with JI-36 was able to revert initial hyperglycemia to normal ranges within 2 hrs. Shaded area highlights normal range of blood glucose. (C) Pancreatic islets were treated with JI-36 prior to transplantation beneath the kidney capsule. Representative immunostained section for insulin (green) shows stable graft integration after 27 days.

For all islet preparations tested, animals transplanted with islets previously exposed to agonist JI-36 consistently performed better, with blood glucose levels reaching the range of normal healthy mice. When evaluated at day 25, 5 of 6 animals from the JI-36 group were "cured", one animal showed partial graft function. In comparison, in the control group, only 3 animals were normoglycemic, two had impaired graft function and one animal showed graft failure (FIG. 7A). In the intraperitoneal glucose tolerance test (IPGTT), the JI-36 group showed an insulin response comparable to that of normal healthy mice, whereas control islets in animals, classified as "cured" on the basis of attaining normoglycemia before challenge, exhibited delayed and inadequate responses to glucose challenge (FIG. 7B).

Islet grafts retrieved on day 27 after transplantation were immunostained for insulin and showed stable graft integration (FIG. 7C).

Discussion:

The main finding of the present study is that GHRH agonist JI-36 improves beta cell survival and growth as well as metabolic function. The expression of mRNA and protein for GHRH in both rodent and human islets was demonstrated. The GHRH agonist reduced programmed cell death of beta cells. This was reversed by an antagonist of GHRH. Finally, pretreatment with GHRH agonist improved beta cell engraftment and metabolic function of islets following transplantation under the kidney capsule in the streptozotocin-induced diabetic mice. Furthermore, islets treated with the GHRH agonist before transplantation into diabetic NOD-SCID mice, were able to produce normoglycemia in these mice earlier and more consistently than islets sham treated without JI-36. In addition, JI-36 exposed islets showed a stronger response upon glucose challenge compared to untreated islets in vitro and in vivo.

GH itself and IGF-1, as well as GH-releasing peptides such as ghrelin and other GH secretagogues, increase beta cell proliferation in transplanted human and fetal rat islets (25, 26). This is, however, the first study demonstrating the potential role of a GHRH agonist in islet cell proliferation and survival. The detection of the GHRH receptor on beta cells in rat and human islets supports the view that GHRH may exert a direct signal transduction within the pancreas independent and/or in addition to the effects mediated by the GH/IGF-1 pathways.

While ghrelin and other GH secretagogues may have pleiotropic actions with potentially unexpected side effects, the administration of GHRH may offer a more physiological approach due to its direct actions. The ultrastructural analysis demonstrated an increase of beta cell cytoplasm with a reduction of cell extensions and filopodia. Interestingly, a recent study has shown a beneficial effect of another hypothalamic releasing hormone, corticotrophin releasing hormone, on beta cell proliferation (27), further emphasizing an important connection between the hypothalamic-pituitary axis and the integrity of insulin producing cells in the pancreas. Synthetic agonists of GHRH such as JI-36 are more potent and longer acting than native GHRH or other growth factors. This may open new therapeutic options. Since there are millions of patients with type 1 diabetes and the availability of pancreatic islet donors is extremely limited, reaching less than a few hundred per year, there is a desperate need for the development of methods for increasing the efficiency of beta cell function and islet cell mass. In vitro expansion of islet cell function and mass by the use of growth factors is therefore of great interest. In vivo treatment with GHRH analogue may have a tremendous impact also on the prevention and treatment of type 2 diabetes patients. A major feature of diabetes mellitus type 2 is the progressive loss of beta cell mass over time, very similar to the situation with transplanted human islets.

By improving the quality of islets and by a careful quality control of the islets prior to transplantation, the results can be substantially improved (2). Furthermore, beta cells are able to replicate under basal conditions and that beta cell mass can be augmented in response to a variety of physiological and/or pathophysiological stimuli (28). Indeed, the major source of new beta cells during adult life is more likely due to the proliferation of pre-existing beta cells than the differentiation of progenitor or stem cells in the pancreas (29). Therefore, improving beta cell function and replication in vivo may be an important therapeutic strategy for both the prevention and the cure of diabetes mellitus. Although this study was mainly performed in rodents, it was also demonstrated that the receptor was expressed in human islet cells. On the basis of previous studies with other growth factors, it is appropriate to extrapolate that human islets will have the same potential to expand and improve islet cell mass in a fashion similar to the results observed in the animal models. In addition to refining quality of islet cells and islet cell function prior to transplantation, it may be possible to improve islet engraftment and reduce the number of islets needed for a successful outcome by using a short-term in vivo exposure to the agonist. Previous work has shown that temporary systemic administration of growth factors such as hepatocyte growth factor (HGF) may improve graft survival and blood glucose control in vivo (30).

In summary, the current long term efficacy of clinical islet transplantation is rather low. One of the major underlying factors for this outcome is the loss of islet mass over time.

Therefore, the exploration of mechanisms promoting islet proliferation and growth is critically important for further progress in the field. The application of synthetic GHRH agonist for islet proliferation in vitro as well as graft function and survival in vivo in therapies of diabetes and the demonstration of the importance of local autocrine and paracrine GHRH in beta cell regulation and growth provide a promising regenerative therapeutic potential for patients with diabetes.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

REFERENCES

1. Shapiro A-M et al. (2006) International trial of the Edmonton protocol for islet transplantation. *N Engl J Med* 355:1318-1330.
2. Armann B, Hanson M-S, Hatch E, Steffen A, Fernandez L-A (2007) Quantification of basal and stimulated ROS levels as predictors of islet potency and function. *Am J Transplant* 7:38-47.
3. Lehmann R, Spinas G-A, Moritz W, Weber M (2008) Has time come for new goals in human islet transplantation? *Am J Transplant* 8:1096-1100.
4. Reimann M et al. (2009) An update on preventive and regenerative therapies in diabetes mellitus. *Pharmacol Ther* 121:317-331.
5. Nielsen J-H, Svensson C, Galsgaard E-D, Moldrup A, Billestrup N (1999) Beta cell proliferation and growth factors. *J Mol Med* 77:62-66.
6. Lingohr M-K, Buettner R, Rhodes C-J (2002) Pancreatic beta-cell growth and survival—a role in obesity-linked type 2 diabetes? *Trends Mol Med* 8:375-384.
7. Granata R et al. (2008) Obestatin promotes survival of pancreatic beta-cells and human islets and induces expression of genes involved in the regulation of beta-cell mass and function. *Diabetes* 57:967-979.
8. Holst J-J (2010) Glucagon and glucagon-like peptides 1 and 2. *Results Probl Cell Differ* 50:121-135.
9. Houssay B-A (1950) [Role of the hypophysis in carbohydrate metabolism and diabetes.]*Folia Endocrinol Mens Incretologia Incretoterapia* 3:127-136.
10. Ling N et al. (1984) Isolation, primary structure, and synthesis of human hypothalamic somatocrinin: growth hormone-releasing factor. *Proc Natl Acad Sci USA* 81:4302-4306.
11. Rivier J, Spiess J, Thorner M, Vale W (1982) Characterization of a growth hormone-releasing factor from a human pancreatic islet tumour. *Nature* 300:276-278.
12. Vance M-L (1990) Growth-hormone-releasing hormone. *Clin Chem* 36:415-420.
13. Guarcello V, Weigent, D-A, Blalock J-E (1991) Growth hormone releasing hormone receptors on thymocytes and splenocytes from rats. *Cell Immunol* 136:291-302.
14. Havt A et al. (2005) The expression of the pituitary growth hormone-releasing hormone receptor and its splice variants in normal and neoplastic human tissues. *Proc Natl Acad Sci USA* 102:17424-17429.
15. Khorram O, Yeung M, Vu L, Yen S-S (1997) Effects of [norleucine27] growth hormone-releasing hormone (GHRH) (1-29)-NH2 administration on the immune system of aging men and women. *J Clin Endocrinol Metab* 82:3590-3596.
16. Kanashiro-Takeuchi R-M et al. (2010) Cardioprotective effects of growth hormone-releasing hormone agonist after myocardial infarction. *Proc Natl Acad Sci USA* 107:2604-2609.
17. Granata R et al. (2009) Growth hormone-releasing hormone promotes survival of cardiac myocytes in vitro and protects against ischaemia-reperfusion injury in rat heart. *Cardiovasc Res* 83:303-312.
18. Izdebski J et al. (1995) Synthesis and biological evaluation of superactive agonists of growth hormone-releasing hormone. *Proc Natl Acad Sci USA* 92:4872-4876.
19. Schally A-V, Comaru-Schally A-M (1998) in *Growth Hormone Secretagogues in Clinical Practice*, eds Bercu B-B, Walker R-F (Marcel Dekker, Inc, New York), pp 131-142.
20. Letsch M, Schally A-V, Busto R, Bajo A-M, Varga J-L (2003) *Proc Natl Acad Sci USA* 100, 1250-5
21. Jabs N et al. (2008) Reduced insulin secretion and content in VEGF-a deficient mouse pancreatic islets. *Exp Clin Endocrinol Diabetes* 116 Suppl 1:S46-49.
22. Nikolova G et al. (2006) The vascular basement membrane: a niche for insulin gene expression and Beta cell proliferation. *Dev Cell* 10:397-405.
23. Rekasi Z, Czompoly T, Schally A-V, Halmos G (2000) Isolation and sequencing of cDNAs for splice variants of growth hormone-releasing hormone receptors from human cancers. *Proc Natl Acad Sci USA* 97:10561-10566.
24. Ziegler C-G et al. (2009) Expression of neuropeptide hormone receptors in human adrenal tumors and cell lines: antiproliferative effects of peptide analogues. *Proc Natl Acad Sci USA* 106:15879-15884.
25. Hoglund E, Mattsson G, Tyrberg B, Andersson A, Carlsson C (2009) Growth hormone increases beta-cell proliferation in transplanted human and fetal rat islets. *Jop* 10:242-248.
26. Vasavada R-C et al. (2006) Growth factors and beta cell replication. *Int J Biochem Cell Biol* 38:931-950.
27. Huising M-O et al. (2009) CRFR1 is expressed on pancreatic beta cells, promotes beta cell proliferation, and potentiates insulin secretion in a glucose-dependent manner. *Proc Natl Acad Sci USA* 107:912-917.
28. Bonner-Weir S et al. (2000) In vitro cultivation of human islets from expanded ductal tissue. *Proc Natl Acad Sci USA* 97:7999-8004.
29. Dor Y, Brown J, Martinez O-I, Melton D-A (2004) Adult pancreatic beta-cells are formed by self-duplication rather than stem-cell differentiation. *Nature* 429:41-46.
30. Fiaschi-Taesch N-M et al. (2008) Hepatocyte growth factor enhances engraftment and function of nonhuman primate islets. *Diabetes* 57:2745-2754.
31. Ricordi C, Lacy P-E, Finke E-H, Olack B-J, Scharp D-W (1988) Automated method for isolation of human pancreatic islets. *Diabetes* 37:413-420.
32. Latif Z-A, Noel J, Alejandro R (1988) A simple method of staining fresh and cultured islets. *Transplantation* 45:827-30.
33. London N-J et al. (1989) A microfluorometric viability assay for isolated human and rat islets of Langerhans. *Diabetes Res* 12:141-149.
34. Ziegler C-G et al. (2008) Dehydroepiandrosterone induces a neuroendocrine phenotype in nerve growth factor-stimulated chromaffin pheochromocytoma PC12 cells. *Endocrinology* 149:320-328.

The invention claimed is:

1. A method of treating a patient diagnosed with diabetes comprising:
exposing islet cells in vitro to an agent selected from growth hormone releasing hormone (GHRH) and an agonist of growth hormone releasing hormone (GHRH);
washing the islet cells after the exposure step to remove the agent;
transplanting the exposed islet cells into a patient; and
administering a therapeutically effective amount to the patient an agent selected from growth hormone releasing hormone (GHRH) and an agonist of growth hormone releasing hormone (GHRH).

2. The method of claim 1, wherein the GHRH is administered pre-transplantation, concurrently with transplantation, post-transplantation or any combinations thereof.

3. The method of claim 1, wherein the agonist of GHRH comprises at least one of JI-34 [Dat$^1$, Orn$^{12,21}$, Abu$^{15}$, Nle$^{27}$, Asp$^{28}$, Agm$^{29}$]hGH-RH(1-29)NH$_2$, JI-36 [Dat$^1$, Thr$^8$, Orn$^{12,21}$, Abu$^{15}$, Nle$^{27}$, Asp$^{28}$, Agm$^{29}$]hGH-RH(1-29)NH$_2$, and/or JI-38 [Dat$^1$, Gln$^8$, Orn$^{12,21}$, Abu$^{15}$, Nle$^{27}$, Asp$^{28}$, Agm$^{29}$]hGH-RH(1-29)NH$_2$.

4. The method of claim 1, wherein the agonist of GHRH is JI-36: [Dat$^1$, Thr$^8$, Orn$^{12,21}$, Abu$^{15}$, Nle$^{27}$, Asp$^{28}$, Agm$^{29}$]hGH-RH(1-29)NH$_2$.

5. The method of claim 1, wherein the islet cells are autologous, allogeneic, xenogeneic, syngeneic, or combinations thereof.

6. The method of claim 1, further comprising administering a therapeutically effective amount of tesamorelin.

7. The method of claim 1, wherein the islet cells comprises tissue comprising islet cells.

8. The method of claim 1, wherein the agonist of GHRH is administered pre-transplantation, concurrently with transplantation, post-transplantation or any combinations thereof.

* * * * *